(12) United States Patent
Makrigiorgos

(10) Patent No.: US 11,174,510 B2
(45) Date of Patent: *Nov. 16, 2021

(54) FULL COLD-PCR ENRICHMENT WITH REFERENCE BLOCKING SEQUENCE

(71) Applicant: Dana-Farber Cancer Institute, Inc., Boston, MA (US)

(72) Inventor: Gerassimos Makrigiorgos, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 604 days.

This patent is subject to a terminal disclaimer.

(21) Appl. No.: 15/940,274

(22) Filed: Mar. 29, 2018

(65) Prior Publication Data

US 2018/0282798 A1 Oct. 4, 2018

Related U.S. Application Data

(63) Continuation of application No. 14/107,291, filed on Dec. 16, 2013, now Pat. No. 9,957,556, which is a continuation of application No. 13/042,549, filed on Mar. 8, 2011, now Pat. No. 8,623,603.

(60) Provisional application No. 61/311,642, filed on Mar. 8, 2010.

(51) Int. Cl.
| *C12Q 1/68* | (2018.01) |
| *C12Q 1/6848* | (2018.01) |
| *C12Q 1/6858* | (2018.01) |

(52) U.S. Cl.
CPC ......... *C12Q 1/6848* (2013.01); *C12Q 1/6858* (2013.01)

(58) Field of Classification Search
CPC ........ C12Q 2537/163; C12Q 2527/107; C12Q 1/6858
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 5,045,450 A | 9/1991 | Thilly et al. |
| 5,075,217 A | 12/1991 | Weber |
| 5,256,775 A | 10/1993 | Froehler |
| 5,399,491 A | 3/1995 | Kacian et al. |
| 5,409,818 A | 4/1995 | Davey et al. |
| 5,427,930 A | 6/1995 | Birkenmeyer et al. |
| 5,541,308 A | 7/1996 | Hogan et al. |
| 5,554,527 A | 9/1996 | Fickenscher |
| 5,565,340 A | 10/1996 | Chenchik et al. |
| 5,612,473 A | 3/1997 | Wu et al. |
| 5,618,703 A | 4/1997 | Gelfand et al. |
| 5,631,147 A | 5/1997 | Lohman et al. |
| 5,648,211 A | 7/1997 | Fraiser et al. |
| 5,656,461 A * | 8/1997 | Demers ............... C12Q 1/686 |
| | | 435/5 |
| 5,744,311 A | 4/1998 | Fraiser et al. |
| 5,792,607 A | 8/1998 | Backman et al. |
| 5,846,710 A | 12/1998 | Bajaj |
| 5,849,497 A | 12/1998 | Steinman |
| 5,994,056 A | 11/1999 | Higuchi |
| 6,030,115 A | 2/2000 | Ishiguro et al. |
| 6,174,680 B1 | 1/2001 | Makrigiorgos |
| 6,197,499 B1 | 3/2001 | Hughes et al. |
| 7,618,773 B2 | 11/2009 | Rand et al. |
| 7,635,566 B2 | 12/2009 | Brenner |
| 8,071,338 B2 | 12/2011 | Newton |
| 8,455,190 B2 | 6/2013 | Makrigiorgos |
| 8,623,603 B2 * | 1/2014 | Makrigiorgos ...... C12Q 1/6858 |
| | | 435/6.12 |
| 8,628,924 B2 | 1/2014 | Kacian et al. |
| 9,133,490 B2 | 9/2015 | Candau-Cachon |
| 9,957,556 B2 * | 5/2018 | Makrigiorgos ...... C12Q 1/6848 |
| 2002/0016680 A1 | 2/2002 | Wang et al. |
| 2002/0045227 A1 | 4/2002 | Wagener |
| 2003/0008286 A1 | 1/2003 | Zou et al. |
| 2003/0092021 A1 | 5/2003 | Thilly |
| 2004/0023207 A1 * | 2/2004 | Polansky ............. A61K 48/005 |
| | | 435/5 |
| 2004/0033518 A1 | 2/2004 | Wittwer et al. |
| 2004/0166519 A1 | 8/2004 | Cargill et al. |
| 2005/0089984 A1 | 4/2005 | Ginns et al. |
| 2006/0063175 A1 | 3/2006 | Xu et al. |

(Continued)

FOREIGN PATENT DOCUMENTS

| CN | 1650028 A | 8/2005 |
| EP | 0370719 A2 | 5/1990 |

(Continued)

OTHER PUBLICATIONS

Extended European Search Report for EP 17881834.0 dated Jun. 16, 2020.

(Continued)

*Primary Examiner* — Teresa E Strzelecka
*Assistant Examiner* — Olayinka A Oyeyemi
(74) *Attorney, Agent, or Firm* — Wolf, Greenfield & Sacks, P.C.

(57) ABSTRACT

The present invention is directed to methods, compositions and software for enriching low abundance alleles in a sample. It is directed in particular to the use of an excess amount of reference blocking sequence in an amplification reaction mixture in order to improve the enrichment efficiency, and reduce cycle time, of full COLD-PCR.

19 Claims, 8 Drawing Sheets

Specification includes a Sequence Listing.

(56) References Cited

U.S. PATENT DOCUMENTS

| | | |
|---|---|---|
| 2007/0020672 A1 | 1/2007 | Wittwer et al. |
| 2007/0154892 A1 | 7/2007 | Wain-Hobson et al. |
| 2008/0269068 A1 | 10/2008 | Church et al. |
| 2010/0173311 A1 | 7/2010 | Grow et al. |
| 2010/0203532 A1 | 8/2010 | Makrigiorgos |
| 2010/0233683 A1 | 9/2010 | Molloy et al. |
| 2011/0217714 A1 | 9/2011 | Makrigiorgos |
| 2012/0225421 A1 | 9/2012 | Richardson et al. |
| 2013/0303385 A1 | 11/2013 | Korlach et al. |
| 2013/0309724 A1 | 11/2013 | Candau-Cachon |
| 2014/0051087 A1 | 2/2014 | Makrigiorgos |
| 2014/0106362 A1 | 4/2014 | Makrigiorgos |
| 2014/0315726 A1 | 10/2014 | Beatty et al. |
| 2015/0147760 A1 | 5/2015 | Gupta et al. |
| 2016/0186237 A1* | 6/2016 | Makrigiorgos ...... C12Q 1/6858 506/9 |
| 2020/0040388 A1 | 2/2020 | Makrigiorgos et al. |

FOREIGN PATENT DOCUMENTS

| | | | |
|---|---|---|---|
| EP | 2004852 B1 | 12/2010 | |
| EP | 2 545 189 A1 | 1/2013 | |
| GB | 2293238 A | 3/1996 | |
| JP | 2005-536983 | 12/2005 | |
| JP | 6-510201 | 9/2012 | |
| JP | 2012-165755 | 5/2019 | |
| WO | 1990/11369 A1 | 10/1990 | |
| WO | WO 1990/13668 A1 | 11/1990 | |
| WO | WO 1991/14003 A2 | 9/1991 | |
| WO | WO 1997/19193 A2 | 5/1997 | |
| WO | WO 1999/14226 A2 | 3/1999 | |
| WO | WO 1999/61661 A1 | 12/1999 | |
| WO | WO 2001/068900 A2 | 9/2001 | |
| WO | WO 2002/018659 A2 | 3/2002 | |
| WO | WO 2002/086155 A2 | 10/2002 | |
| WO | WO 2003/072809 A1 | 9/2003 | |
| WO | WO 2005/093101 A1 | 10/2005 | |
| WO | WO 2007/047572 A2 | 4/2007 | |
| WO | WO 2007/087310 A2 | 8/2007 | |
| WO | WO 2007/106534 A2 | 9/2007 | |
| WO | WO 2009/017784 A2 | 2/2009 | |
| WO | WO 2009/019008 A1 | 2/2009 | |
| WO | WO-2009019008 A1 * | 2/2009 | ........... C12Q 1/6858 |
| WO | WO 2010/065626 A1 | 6/2010 | |
| WO | WO 2011/112534 A1 | 9/2011 | |
| WO | WO-2011112534 A1 * | 9/2011 | ........... C12Q 1/6848 |
| WO | WO 2012/129363 A2 | 9/2012 | |
| WO | WO 2012/135664 A2 | 10/2012 | |
| WO | WO 2012/159089 A1 | 11/2012 | |
| WO | WO 2014/142261 A1 | 9/2014 | |

OTHER PUBLICATIONS

Bunyan et al., Different denaturation rates between methylated and non-methylated genomic DNA can result in allele-specific PCR amplification. Open J. Gen. Sep. 2011;1:13-14.
Ladas et al., Multiplexed Elimination of Wild-Type DNA and High-Resolution Melting Prior to Targeted Resequencing of Liquid Biopsies. Clin Chem. 2017;63(10):1605-1613. doi:10.1373/clinchem. 2017.272849.
Riesewijk et al., Monoallelic expression of human PEG1/MEST is paralleled by parent-specific methylation in fetuses. Genomics. Jun. 1, 1997;42(2):236-44.
Walsh et al., Preferential PCR amplification of alleles: mechanisms and solutions. PCR Methods Appl. May 1992;1(4):241-50.
Partial Supplementary European Search Report for EP12764286.6 dated Nov. 17, 2014.
Extended European Search Report for EP12764286.6 dated Mar. 18, 2015.
Extended European Search Report for EP 17196718.5 dated May 14, 2018.
International Preliminary Report on Patentability for PCT/EP2008/006476 dated Feb. 9, 2010.
International Search Report and Written Opinion for PCT/US2008/009248 dated Jan. 6, 2009.
International Preliminary Report on Patentability for PCT/US2008/009248 dated Feb. 2, 2010.
International Search Report and Written Opinion for PCT/US2011/027473 dated Jun. 28, 2011.
International Preliminary Report on Patentability for PCT/US2011/027473 dated Sep. 20, 2012.
Invitation to Pay Additional Fees for PCT/US2012/031527 dated Aug. 28, 2012.
International Search Report and Written Opinion for PCT/US2012/031527 dated Nov. 5, 2012.
International Preliminary Report on Patentability for PCT/US2012/031527 dated Oct. 10, 2013.
International Search Report and Written Opinion for PCT/US2014/047373 dated Nov. 12, 2014.
International Preliminary Report on Patentability for PCT/US2014/047373 dated Feb. 4, 2016.
Canadian Application Serial No. 2,792,433, Office Action dated Feb. 5, 2014, 3 pgs.
Canadian Application Serial No. 2,792,433, Office Action dated Mar. 18, 2015, 3 pgs.
Canadian Application Serial No. 2,792,433, Response filed Aug. 5, 2014 to Office Action dated Feb. 5, 2014, 17 pgs.
European Application Serial No. 11709836.8, Office Action dated Oct. 26, 2014, 4 pgs.
European Application Serial No. 11709836.8, Office Action dated Nov. 7, 2012, 2 pgs.
European Application Serial No. 11709836.8, Response filed May 17, 2013 to Office Action ated Nov. 7, 2012, 9 pgs.
Japanese Application Serial No. 2012-557157, Office Action dated Feb. 18, 2015, 3 pgs.
Korean Application Serial No. 10-2012-7026077, Amendment filed Oct. 20, 2014, 9 pgs.
Korean Application Serial No. 10-2012-7026077, Notice dated Feb. 27, 2015 (w/ English Translation), 5 pgs.
Korean Application Serial No. 10-2012-7026077, Request for Reconsideration and Response filed May 29, 2015 (w/ English Translation of Claims), 20 pgs.
[No Author Listed] BioMath Calculators: Tm Calculation for Oligos. Last accessed Oct. 27, 2014 from https://www.promega.com/techserv/tools/biomath/calc 11.htm.
[No Author Listed] COLD-PCR: Very High Sensitivity Mutation Detection. Transgenomic. Jul. 1, 2010: 31 pages. Last accessed at <http://www.transgenomic.com/files/literature/48227300.pdf> on Oct. 25, 2014.
[No Author Listed] Integrated DNA Technologies Molecular Facts and Figures [online] [retrieved on Feb. 17, 2015] retrieved from https://www.idtdna.com/pages/docs/educational-resources/molecular-facts-and-figures.pdf?sfvrsn=4.
[No Author Listed] User Guide for the REVEAL Kit KRAS Exon 2. A Mutation Enrichment Assay Powered by ICE COLD-PCR. Transgenomic, Inc 2012.
Ahmadian et al., Pyrosequencing: history, biochemistry and future. Clin Chim Acta. Jan. 2006;363(1-2):83-94. Epub Sep. 13, 2005.
Ahrendt et al., p53 mutations and survival in stage I non-small-cell lung cancer: results of a prospective study. J Natl Cancer Inst. Jul. 2, 2003;95(13):961-70.
Altschul et al., Gapped BLAST and PSI-BLAST: a new generation of protein database search programs. Nucleic Acids Res. Sep. 1, 1997;25(17):3389-402.
Amicarelli et al., FLAG assay as a novel method for real-time signal generation during PCR: application to detection and genotyping of KRAS codon 12 mutations. Nucleic Acids Res. 2007;35(19):e131. Epub Oct. 11, 2007.
Aoki et al., Liposome-mediated in vivo gene transfer of antisense K-ras construct inhibits pancreatic tumor dissemination in the murine peritoneal cavity. Cancer Res. Sep. 1, 1995;55(17):3810-6.
Armour et al., Recent advances in minisatellite biology. FEBS Lett. Jul. 27, 1992;307(1):113-5.

(56) References Cited

OTHER PUBLICATIONS

Beaucage et al., Deoxynucleoside phosphoramidites—A new class of key intermediates for deoxypolynucleotide synthesis. Tetrahedron Letters. 1981;22(20):1859-62. doi:10.1016/S00404039(01)90461-7.

Beau-Faller et al., Detection of K-Ras mutations in tumour samples of patients with non-small cell lung cancer using PNA-mediated PCR clamping. Br J Cancer. Mar. 24, 2009;100(6):985-92. doi:10.1038/sj.bjc.6604925.

Behn et al., Simple and reliable factor V genotyping by PNA-mediated PCR clamping. Thromb Haemost. Apr. 1998;79(4):773-7.

Belinsky et al., Gene promoter methylation in plasma and sputum increases with lung cancer risk. Clin Cancer Res. Sep. 15, 2005;11(18):6505-11.

Bi et al., Detection of known mutation by proof-reading PCR. Nucleic Acids Res. Jun. 15, 1998;26(12):3073-5.

Blake et al., Thermal stability of DNA. Nucleic Acids Res. Jul. 15, 1998;26(14):3323-32.

Boisselier et al., COLD PCR HRM: a highly sensitive detection method for IDH1 mutations. Hum Mutat. Dec. 2010;31(12):1360-5. doi: 10.1002/humu.21365. Epub Nov. 9, 2010.

Botstein et al., Construction of a genetic linkage map in man using restriction fragment length polymorphisms. Am J Hum Genet. May 1980;32(3):314-31.

Braasch et al., Locked nucleic acid (LNA): fine-tuning the recognition of DNA and RNA. Chem Biol. Jan. 2001;8(1):1-7.

Candau et al., Very High Sensitivity Detection of K-RAS Exon 2 Mutations Using Fast COLD-PCR. AACR 2010 Poster Presentation.

Castellanos-Rizaldos et al., Temperature-tolerant COLD-PCR reduces temperature stringency and enables robust mutation enrichment. Clin Chem. Jul. 2012;58(7):1130-8. doi: 10.1373/clinchem.2012.183095. Epub May 15, 2012.

Chakrabarti et al., Highly selective isolation of unknown mutations in diverse DNA fragments: toward new multiplex screening in cancer. Cancer Res. Jul. 15, 2000;60(14):3732-7.

Chen et al., Fetal DNA analyzed in plasma from a mother's three consecutive pregnancies to detect paternally inherited aneuploidy. Clin Chem. May 2001;47(5):937-9.

Chiu et al., Hypermethylation of RASSF1A in human and rhesus placentas. Am J Pathol. Mar. 2007;170(3):941-50.

Chou et al., A comparison of high-resolution melting analysis with denaturing high-performance liquid chromatography for mutation scanning: cystic fibrosis transmembrane conductance regulator gene as a model. Am J Clin Pathol. Sep. 2005;124(3):330-8.

Chow et al., Mass spectrometric detection of an SNP panel as an internal positive control for fetal DNA analysis in maternal plasma. Clin Chem. Jan. 2007;53(1):141-2.

Compton, Nucleic acid sequence-based amplification. Nature. Mar. 7, 1991;350(6313):91-2.

Corless et al., Allele-specific polymerase chain reaction for the imatinib-resistant KIT D816V and D816F mutations in mastocytosis and acute myelogenous leukemia. J Mol Diag Nov. 2006;8(5):604-612.

Coutelle, New DNA-analysis techniques (minireview). Biomed Biochim Acta. 1991;50(1):3-10.

Däbritz et al., Detection of Ki-ras mutations in tissue and plasma samples of patients with pancreatic cancer using PNA-mediated PCR clamping and hybridisation probes. Br J Cancer. Jan. 31, 2005;92(2):405-12.

Delaney et al., GNAS1 mutations occur more commonly than previously thought in intramuscular myxoma. Mod Pathol. May 2009;22(5):718-24. doi: 10.1038/modpathol.2009.32. Epub Mar. 13, 2009.

Di Fiore et al., Clinical relevance of KRAS mutation detection in metastatic colorectal cancer treated by Cetuximab plus chemotherapy. Br J Cancer. Apr. 23, 2007;96(8):1166-9. Epub Mar. 20, 2007.

Diehl et al., BEAMing: single-molecule PCR on microparticles in water-in-oil emulsions. Nat Methods. Jul. 2006;3(7):551-9.

Diehl et al., Circulating mutant DNA to assess tumor dynamics. Nat Med. Sep. 2008;14(9):985-90. doi:10.1038/nm.1789. Epub Jul. 31, 2007.

Diehl et al., Detection and quantification of mutations in the plasma of patients with colorectal tumors. Proc Natl Acad Sci U S A. Nov. 8, 2005;102(45):16368-73. Epub Oct. 28, 2005.

Dif-Couvreux et al., [Evaluation of conventional hemi nested PCR analysis for fetal RHD determination in maternal plasma]. J Gynecol Obstet Biol Reprod (Paris). Nov. 2006;35(7):658-64. French.

Dominguez et al., Wild-type blocking polymerase chain reaction for detection of single nucleotide minority mutations from clinical specimens. Oncogene. Oct. 13, 2005;24(45):6830-4. Erratum in: Oncogene. Jan. 26, 2006;25(4):656.

Dressman et al., Transforming single DNA molecules into fluorescent magnetic particles for detection and enumeration of genetic variations. Proc Natl Acad Sci U S A. Jul. 22, 2003;100(15):8817-22. Epub Jul. 11, 2003.

Eberhard et al., Mutations in the epidermal growth factor receptor and in KRAS are predictive and prognostic indicators in patients with non-small-cell lung cancer treated with chemotherapy alone and in combination with erlotinib. J Clin Oncol. Sep. 1, 2005;23(25):5900-9. Epub Jul. 25, 2005.

Engelman et al., Allelic dilution obscures detection of a biologically significant resistance mutation in EGFR-amplified lung cancer. J Clin Invest. Oct. 2006;116(10):2695-706. Epub Aug. 10, 2006.

Fan et al., A versatile assay for high-throughput gene expression profiling on universal array matrices. Genome Res. May 2004;14(5):878-85.

Frommer et al., A genomic sequencing protocol that yields a positive display of 5-methylcytosine residues in individual DNA strands. Proc Natl Acad Sci U S A. Mar. 1, 1992;89(5):1827-31.

Fuery et al., Detection of rare mutant alleles by restriction endonuclease-mediated selective-PCR: assay design and optimization. Clin Chem. May 2000;46(5):620-4.

Galbiati et al., Novel use of Full COLD-PCR protocol for noninvasive prenatal diagnosis of genetic diseases. Clin Chem. Jan. 2011;57(1):136-8. doi: 10.1373/clinchem.2010.155671. Epub Oct. 25, 2010.

Genbank Accession No. L32764.1—Human coagulation factor v gene, exon 10 (GI: 488093, submitted Nov. 10, 1994, retrieved on Feb. 16, 2015 from http://www.ncbi.nlm.nih.gov/nuccore/L32764.1).

Giesendorf et al., Molecular beacons: a new approach for semiautomated mutation analysis. Clin Chem. Mar. 1998;44(3):482-6.

Gonzalez et al., Microsatellite alterations and TP53 mutations in plasma DNA of small-cell lung cancer patients: follow-up study and prognostic significance. Ann Oncol. Sep. 2000;11(9):1097-104.

Gray, Cancer: Genomics of metastasis. Nature. Apr. 15, 2010;464(7291):989-90. doi:10.1038/464989a.

Greenman et al., Patterns of somatic mutation in human cancer genomes. Nature. Mar. 8, 2007;446(7132):153-8.

Grossi et al., Prognostic significance of K-ras, p53, bcl-2, PCNA, CD34 in radically resected non-small cell lung cancers. Eur J Cancer. Jun. 2003;39(9):1242-50.

Guatelli et al., Isothermal, in vitro amplification of nucleic acids by a multienzyme reaction modeled after retroviral replication. Proc Natl Acad Sci U S A. Mar. 1990;87(5):1874-8. Erratum in: Proc Natl Acad Sci U S A Oct. 1990;87(19):7797.

Gundry et al., Amplicon melting analysis with labeled primers: a closed-tube method for differentiating homozygotes and heterozygotes. Clin Chem. Mar. 2003;49(3):396-406.

Gyllensten et al., Generation of single-stranded DNA by the polymerase chain reaction and its application to direct sequencing of the HLA-DQA locus. Proc Natl Acad Sci U S A. Oct. 1988;85(20):7652-6.

Henikoff et al., Amino acid substitution matrices from protein blocks. Proc Natl Acad Sci U S A. Nov. 15, 1992;89(22):10915-9.

Hibi et al., Molecular detection of genetic alterations in the serum of colorectal cancer patients. Cancer Res. Apr. 1, 1998;58(7):1405-7.

Huang et al., Mutations in exon 7 and 8 of p53 as poor prognostic factors in patients with non-small cell lung cancer. Oncogene. May 14, 1998;16(19):2469-77.

(56) References Cited

OTHER PUBLICATIONS

Huang et al., Mutations of p53 and K-ras genes as prognostic factors for non-small cell lung cancer. Int J Oncol. Mar. 1998;12(3):553-63.

Igloi, Variability in the stability of DNA-peptide nucleic acid (PNA) single-base mismatched duplexes: real-time hybridization during affinity electrophoresis in PNA-containing gels. Proc Natl Acad Sci U S A. Jul. 21, 1998;95(15):8562-7.

Jackson et al., Specific p53 mutations detected in plasma and tumors of hepatocellular carcinoma patients by electrospray ionization mass spectrometry. Cancer Res. Jan. 1, 2001;61(1):33-5.

Jänne et al., A rapid and sensitive enzymatic method for epidermal growth factor receptor mutation screening. Clin Cancer Res. Feb. 1, 2006;12(3 Pt 1):751-8.

Jeffreys et al., DNA enrichment by allele-specific hybridization (DEASH): a novel method for haplotyping and for detecting low-frequency base substitutional variants and recombinant DNA molecules. Genome Res. Oct. 2003;13(10):2316-24.

Kanehisa, Use of statistical criteria for screening potential homologies in nucleic acid sequences. Nucleic Acids Res. Jan. 11, 1984;12(1 Pt 1):203-13.

Karlin et al., Applications and statistics for multiple high-scoring segments in molecular sequences. Proc Natl Acad Sci U S A. Jun. 15, 1993;90(12):5873-7.

Khrapko et al., Constant denaturant capillary electrophoresis (CDCE): a high resolution approach to mutational analysis. Nucleic Acids Res. Feb. 11, 1994;22(3):364-9.

Kimura et al., Mutant DNA in plasma of lung cancer patients: potential for monitoring response to therapy. Ann N Y Acad Sci. Jun. 2004;1022:55-60.

Kopreski et al., Somatic mutation screening: identification of individuals harboring K-ras mutations with the use of plasma DNA. J Natl Cancer Inst. Jun. 7, 2000;92(11):918-23.

Kosaka et al., Mutations of the epidermal growth factor receptor gene in lung cancer: biological and clinical implications. Cancer Res. Dec. 15, 2004;64(24):8919-23.

Koshkin et al., LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron. 1998;54(14):3607-30. doi:10.1016/s00404020(98)00094-5.

Kulinski et al., Comparative calorimetric studies on the dynamic conformation of plant 5S rRNA: II. Structural interpretation of the thermal unfolding patterns for lupin seeds and wheat germ. Nucleic Acids Res. May 11, 1991;19(9):2449-55.

Kwoh et al., Transcription-based amplification system and detection of amplified human immunodeficiency virus type 1 with a bead-based sandwich hybridization format. Proc Natl Acad Sci U S A. Feb. 1989;86(4): 1173-7.

Kwok, Finding a needle in a haystack: detection and quantification of rare mutant alleles are coming of age. Clin Chem. May 2000;46(5):593-4.

Kwok, High-throughput genotyping assay approaches. Pharmacogenomics. Feb. 2000;1(1):95-100.

Lander et al., Mapping mendelian factors underlying quantitative traits using RFLP linkage maps. Genetics. Jan. 1989;121(1):185-99. Erratum in: Genetics Feb. 1994;136(2):705.

Latorra et al., Enhanced allele-specific PCR discrimination in SNP genotyping using 3' locked nucleic acid (LNA) primers. Hum Mutat. Jul. 2003;22(1):79-85.

Lázaro et al., Mutation analysis of genetic diseases by asymmetric-PCR SSCP and ethidium bromide staining: application to neurofibromatosis and cystic fibrosis. Mol Cell Probes. Oct. 1992;6(5):357-9.

Li et al., BEAMing up for detection and quantification of rare sequence variants. Nat Methods. Feb. 2006;3(2):95-7.

Li et al., Coamplification at lower denaturation temperature—PCR increases mutation-detection selectivity of TaqMan-based real-time PCR. Clin Chem. Apr. 2009;55(4):748-56. doi:10.1373/clinchem.2008.113381. Epub Feb. 20, 2009.

Li et al., COLD-PCR: a new platform for highly improved mutation detection in cancer and genetic testing. Biochem Soc Trans. Apr. 2009;37(Pt 2):427-32. doi: 10.1042/BST0370427.

Li et al., Multiplex padlock targeted sequencing reveals human hypermutable CpG variations. Genome Res. Sep. 2009;19(9):1606-15. doi: 10.1101/gr.092213.109. Epub Jun. 12, 2009.

Li et al., Replacing PCR with COLD-PCR enriches variant DNA sequences and redefines the sensitivity of genetic testing. Nat Med. May 2008;14(5):579-84. doi: 10.1038/nm1708. Epub Apr. 13, 2008.

Li et al., s-RT-MELT for rapid mutation scanning using enzymatic selection and real time DNA-melting: new potential for multiplex genetic analysis. Nucleic Acids Res. 2007;35(12):e84. Epub Jun. 1, 2007.

Li et al., Two-round coamplification at lower denaturation temperature-PCR (COLD-PCR)-based sanger sequencing identifies a novel spectrum of low-level mutations in lung adenocarcinoma. Hum Mutat. Nov. 2009;30(11):1583-90. doi: 10.1002/humu.21112.

Liew et al., Genotyping of single-nucleotide polymorphisms by high-resolution melting of small amplicons. Clin Chem. Jul. 2004;50(7):1156-64.

Lipsky et al., DNA melting analysis for detection of single nucleotide polymorphisms. Clin Chem. Apr. 2001;47(4):635-44.

Li-Sucholeiki et al., A sensitive scanning technology for low frequency nuclear point mutations in human genomic DNA. Nucleic Acids Res. May 1, 2000;28(9):E44.

Liu et al., Denaturing high performance liquid chromatography (DHPLC) used in the detection of germline and somatic mutations. Nucleic Acids Res. Mar. 15, 1998;26(6):1396-400.

Liu et al., Detection of hotspot mutations and polymorphisms using an enhanced PCR-RFLP approach. Hum Mutat. May 2003;21(5):535-41.

Liu et al., Inverse PCR-based RFLP scanning identifies low-level mutation signatures in colon cells and tumors. Cancer Res. Apr. 1, 2004;64(7):2544-51.

Luo et al., Detection of rare mutant K-ras DNA in a single-tube reaction using peptide nucleic acid as both PCR clamp and sensor probe. Nucleic Acids Res. Jan. 23, 2006;34(2):e12.

Luthra et al., COLD-PCR finds hot application in mutation analysis. Clin Chem. Dec. 2009;55(12):2077-8. doi: 10.1373/clinchem.2009.136143. Epub Oct. 15, 2009.

Makrigiorgos, PCR-based detection of minority point mutations. Hum Mutat. May 2004;23(5):406-12.

Mamon et al., Preferential amplification of apoptotic DNA from plasma: potential for enhancing detection of minor DNA alterations in circulating DNA. Clin Chem. Sep. 2008;54(9):1582-4. doi:10.1373/clinchem.2008.104612.

Mancini et al., The use of COLD-PCR and high-resolution melting analysis improves the limit of detection of KRAS and BRAF mutations in colorectal cancer. J Mol Diagn. Sep. 2010;12(5):705-11. doi: 10.2353/jmoldx.2010.100018. Epub Jul. 8, 2010.

Mao et al., Synthesis of radioactive single-stranded DNA probes using asymmetrical PCR and oligonucleotide random priming. Biotechniques. Oct. 1999;27(4):674-6, 678.

Margulies et al., Genome sequencing in microfabricated high-density picolitre reactors. Nature. Sep. 15, 2005;437(7057):376-80. Epub Jul. 31, 2005. Erratum in: Nature. May 4, 2006;441(7089):120. Ho, Chun He [corrected to Ho, Chun Heen].

Maulik et al., Novel non-isotopic detection of MutY enzyme-recognized mismatches in DNA via ultrasensitive detection of aldehydes. Nucleic Acids Res. Mar. 1, 1999;27(5):1316-22.

Mayall et al., Mutations of p53 gene can be detected in the plasma of patients with large bowel carcinoma. J Clin Pathol.Aug. 1998;51(8):611-3.

Milbury et al., COLD-PCR-enhanced high-resolution melting enables rapid and selective identification of low-level unknown mutations. Clin Chem. Dec. 2009;55(12):2130-43. doi: 10.1373/clinchem.2009.131029. Epub Oct. 8, 2009.

Milbury et al., Ice-COLD-PCR enables rapid amplification and robust enrichment for low-abundance unknown DNA mutations. Nucleic Acids Res. Jan. 2011;39(1):e2. doi: 10.1093/nar/gkq899. Epub Oct. 11, 2010.

Milbury et al., Multiplex amplification coupled with COLD-PCR and high resolution melting enables identification of low-abundance

(56) References Cited

OTHER PUBLICATIONS mutations in cancer samples with low DNA content. J Mol Diagn. Mar. 2011;13(2):220-32. doi: 10.1016/j.jmoldx.2010.10.008.

Milbury et al., PCR-based methods for the enrichment of minority alleles and mutations. Clin Chem. Apr. 2009;55(4):632-40. doi:10.1373/clinchem.2008.113035. Epub Feb. 6, 2009.

Mitra et al., Digital genotyping and haplotyping with polymerase colonies. Proc Natl Acad Sci U S A. May 13, 2003;100(10):5926-31. Epub May 2, 2003.

Mitra et al., Fluorescent in situ sequencing on polymerase colonies. Anal Biochem. Sep. 1, 2003;320(1):55-65. Erratum in: Anal Biochem. May 15, 2004;328(2):245.

Mitsudomi et al., Prognostic significance of p53 alterations in patients with non-small cell lung cancer: a meta-analysis. Clin Cancer Res. Oct. 2000;6(10):4055-63.

Montgomery et al., Simultaneous mutation scanning and genotyping by high-resolution DNA melting analysis. Nat Protoc. 2007;2(1):59-66.

Murakami et al., p53 gene mutations are associated with shortened survival in patients with advanced non-small cell lung cancer: an analysis of medically managed patients. Clin Cancer Res. Feb. 2000;6(2):526-30.

Nagai et al., Development of a microchamber array for picoliter PCR. Anal Chem. Mar. 1, 2001;73(5):1043-7.

Nagai et al., High-throughput PCR in silicon based microchamber array. Biosens Bioelectron. Dec. 2001;16(9-12):1015-9.

Nickerson et al., Random mutagenesis-PCR to introduce alterations into defined DNA sequences for validation of SNP and mutation detection methods. Hum Mutat. Mar. 2001;17(3):210-9.

Nollau et al., Methods for detection of point mutations: performance and quality assessment. IFCC Scientific Division, Committee on Molecular Biology Techniques. Clin Chem. Jul. 1997;43(7):1114-28.

Obika et al., Stability and structural features of the duplexes containing nucleoside analogues with a fixed N-type conformation, 2'-O,4'-C-methyleneribonucleosides. Tetrahedron Lett. 1998;39:5401-4.

Ogino et al., Sensitive sequencing method for KRAS mutation detection by Pyrosequencing. J Mol Diagn. Aug. 2005;7(3):413-21.

Oldenburg et al., Selective amplification of rare mutations using locked nucleic acid oligonucleotides that competitively inhibit primer binding to wild-type DNA. J Invest Dermatol. Feb. 2008;128(2):398-402. Epub Jun. 21, 2007.

Orita et al., Rapid and sensitive detection of point mutations and DNA polymorphisms using the polymerase chain reaction. Genomics. Nov. 1989;5(4):874-9.

Orum et al., Single base pair mutation analysis by PNA directed PCR clamping. Nucleic Acids Res. Nov. 25, 1993;21(23):5332-6.

Orum, PCR clamping. Curr Issues Mol Biol. Jan. 2000;2(1):27-30.

Paez et al., EGFR mutations in lung cancer: correlation with clinical response to gefitinib therapy. Science. Jun. 4, 2004;304(5676):1497-500. Epub Apr. 29, 2004.

Paner et al., Analysis of melting transitions of the DNA hairpins formed from the oligomer sequences d[GGATAC(X)4GTATCC] (X=A, T, G, C). Biopolymers. Dec. 1990;29(14):1715-34.

Pearson et al., Improved tools for biological sequence comparison. Proc Natl Acad Sci U S A. Apr. 1988;85(8):2444-8.

Persson et al., Four-color multiplex reverse transcription polymerase chain reaction—overcoming its limitations. Anal Biochem. Sep. 1, 2005;344(1):33-42.

Petrie et al., Deep sequencing analysis of mutations resulting from the incorporation of dNTP analogs. Nucleic Acids Res. Dec. 2010;38(22):8095-104. doi:10.1093/nar/gkq685. Epub Aug. 6, 2010.

Pinzani et al., BRAFV600E detection in melanoma is highly improved by COLD-PCR. Clin Chim Acta. May 12, 2011;412(11-12):901-5. doi: 10.1016/j.cca.2011.01.014. Epub Jan. 22, 2011.

Pomp et al., Organic solvents as facilitators of polymerase chain reaction. Biotechniques. Jan. 1991;10(1):58-9.

Porreca et al., Polony DNA sequencing. Curr Protoc Mol Biol. Nov. 2006;Chapter 7:Unit 7.8. doi: 10.1002/0471142727.mb0708s76.

Qin et al., Ultra deep sequencing detects a low rate of mosaic mutations in tuberous sclerosis complex. Hum Genet. Mar. 2010;127(5):573-82. doi: 10.1007/s00439-010-0801-z. Epub Feb. 18, 2010.

Raja et al., Temperature-controlled primer limit for multiplexing of rapid, quantitative reverse transcription-PCR assays: application to intraoperative cancer diagnostics. Clin Chem. Aug. 2002;48(8):1329-37.

Reed et al., Sensitivity and specificity of single-nucleotide polymorphism scanning by high-resolution melting analysis. Clin Chem. Oct. 2004;50(10):1748-54. Epub Aug. 12, 2004.

Rehbein et al., Comparison of different methods to produce single-strand DNA for identification of canned tuna by single-strand conformation polymorphism analysis. Electrophoresis. Jun. 1998;19(8-9):1381-4.

Saiki et al., Enzymatic amplification of beta-globin genomic sequences and restriction site analysis for diagnosis of sickle cell anemia. Science. Dec. 20, 1985;230(4732):1350-4.

Sanchez et al., Two-temperature LATE-PCR endpoint genotyping. BMC Biotechnol. Dec. 4, 2006;6:44.

Saunders et al., Interlaboratory study on thermal cycler performance in controlled PCR and random amplified polymorphic DNA analyses. Clin Chem. Jan. 2001;47(1):47-55.

Schuermann et al., PNA clamping techniques for the determination of oncogene mutations. Methods Mol Biol. 2002;208:165-79.

Schuermann, Detection of K-ras and p53 mutations by "mutant-enriched" PCR-RFLP. Methods Mol Med. 2003;75:325-33.

Seyama et al., A novel blocker-PCR method for detection of rare mutant alleles in the presence of an excess amount of normal DNA. Nucleic Acids Res. May 25, 1992;20(10):2493-6.

Shah et al., Mutational evolution in a lobular breast tumour profiled at single nucleotide resolution. Nature. Oct. 8, 2009;461(7265):809-13. doi: 10.1038/nature08489.

Shao et al., p53 mutation in plasma DNA and its prognostic value in breast cancer patients. Clin Cancer Res. Aug. 2001;7(8):2222-7. Retraction in: Shao ZM, Wu J, Shen ZZ, Nguyen M. Clin Cancer Res. Sep. 2002;8(9):3027.

Shi et al., Ultra-sensitive detection of BRAF V600E and G469A mutations by ICE COLD-PCR and BLOCKer sequencing. Sep. 2011 Poster.

Shi et al., Use of BLOCker Sequencing (BLocking Oligonucleotide Cycle Sequencing) after Ice COLD-PCR for detection of K-RAS and BRAF mutations. May 2011 Poster.

Shigematsu et al., Clinical and biological features associated with epidermal growth factor receptor gene mutations in lung cancers. J Natl Cancer Inst. Mar. 2, 2005;97(5):339-46.

Silva et al., Tumor DNA in plasma at diagnosis of breast cancer patients is a valuable predictor of disease-free survival. Clin Cancer Res. Dec. 2002;8(12):3761-6.

Smith et al., Comparison of biosequences. Adv Appl Math. Dec. 1981;2(4):482-9. doi:10.1016/01968858(81)90046-4.

Steger, Thermal denaturation of double-stranded nucleic acids: prediction of temperatures critical for gradient gel electrophoresis and polymerase chain reaction. Nucleic Acids Res. Jul. 25, 1994;22(14):2760-8.

Sun et al., Detection of tumor mutations in the presence of excess amounts of normal DNA. Nat Biotechnol. Feb. 2002;20(2):186-9.

Suspène et al., Inversing the natural hydrogen bonding rule to selectively amplify GC-rich ADAR-edited RNAs. Nucleic Acids Res. Jul. 2008;36(12):e72. doi: 10.1093/nar/gkn295. Epub May 30, 2008.

Tang et al., Characterization of mitochondrial DNA heteroplasmy using a parallel sequencing system. Biotechniques. Apr. 2010;48(4):287-96. doi:10.2144/000113389.

Thomas et al., High-throughput oncogene mutation profiling in human cancer. Nat Genet. Mar. 2007;39(3):347-51. Epub Feb. 11, 2007. Erratum in: Nat Genet. Apr. 2007;39(4):567. Macconnaill, Laura E [corrected to MacConaill, Laura].

Thomas et al., Sensitive mutation detection in heterogeneous cancer specimens by massively parallel picoliter reactor sequencing. Nat Med. Jul. 2006;12(7):852-5. Epub Jun. 25, 2006. Erratum in: Nat Med. Oct. 2006;12(10):1220.

(56) References Cited

OTHER PUBLICATIONS

Till et al., High-throughput discovery of rare human nucleotide polymorphisms by Ecotilling. Nucleic Acids Res. Aug. 7, 2006;34(13):e99. Erratum in: Nucleic Acids Res. 2006;34(18):5352.

Tong et al., Diagnostic developments involving cell-free (circulating) nucleic acids. Clin Chim Acta. Jan. 2006;363(1-2):187-96. Epub Aug. 26, 2005.

Tsang et al., Circulating nucleic acids in plasma/serum. Pathology. Apr. 2007;39(2):197-207.

Vámosi et al., The helix-coil transition of DNA duplexes and hairpins observed by multiple fluorescence parameters. Biochemistry. Oct. 6, 1998;37(40):14300-16.

Vestheim et al., Blocking primers to enhance PCR amplification of rare sequences in mixed samples—a case study on prey DNA in Antarctic krill stomachs. Front Zool. Jul. 20, 2008;5:12. doi:10.1186/1742-9994-5-12.

Völker et al., High-resolution calorimetric and optical melting profiles of DNA plasmids: resolving contributions from intrinsic melting domains and specifically designed inserts. Biopolymers. Sep. 1999;50(3):303-18. Erratum in: Biopolymers Jan. 2000;53(1):112.

Wagner et al., Challenges for biomarkers in cancer detection. Ann N Y Acad Sci. Jun. 2004;1022:9-16.

Walker et al., Strand displacement amplification—an isothermal, in vitro DNA amplification technique. Nucleic Acids Res. Apr. 11, 1992;20(7):1691-6.

Wang et al., Determination of human beta(2)-adrenoceptor haplotypes by denaturation selective amplification and subtractive genotyping. Am J Pharmacogenomics. 2001;1(4):315-22.

Wetmur, DNA probes: applications of the principles of nucleic acid hybridization. Crit Rev Biochem Mol Biol. 1991;26(3-4):227-59.

Wittwer et al., High-resolution genotyping by amplicon melting analysis using LCGreen. Clin Chem. Jun. 2003;49(6 Pt 1):853-60.

Wittwer et al., The LightCycler: a microvolume multisample fluorimeter with rapid temperature control. Biotechniques. Jan. 1997;22(1):176-81.

Worm et al., In-tube DNA methylation profiling by fluorescence melting curve analysis. Clin Chem. 2001;47(7):1183-9.

Xu et al., Dual primer emulsion PCR for next-generation DNA sequencing. Biotechniques. May 2010;48(5):409-12. doi: 10.2144/000113423.

Yeung et al., Enzymatic mutation detection technologies. Biotechniques. May 2005;38(5):749-58.

Zhang et al., An amplification and ligation-based method to scan for unknown mutations in DNA. Hum Mutat. Aug. 2002;20(2):139-47.

Zhao et al., p53 gene mutations in non-small cell lung cancer detected by polymerase chain reaction single-strand conformation polymorphism analysis. Chin Med Sci J. Sep. 1999;14(3):134-7.

Zhou et al., Closed-tube genotyping with unlabeled oligonucleotide probes and a saturating DNA dye. Clin Chem. Aug. 2004;50(8):1328-35. Epub May 27, 2004.

Zuo et al., Application of COLD-PCR for improved detection of KRAS mutations in clinical samples. Mod Pathol. Aug. 2009;22(8):1023-31. doi:10.1038/modpathol.2009.59. Epub May 8, 2009.

PCT/US2020/047098, Feb. 2, 2021, International Search Report and Written Opinion.

PCT/US2020/047098, Nov. 9, 2020, Invitation to Pay Additional Fees.

International Search Report and Written Opinion for PCT/US2020/047098, dated Feb. 2, 2021.

Invitation to Pay Additional Fees for PCT/US2020/047098, dated Nov. 9, 2020.

Owczarzy et al., Predicting stability of DNA duplexes in solutions containing magnesium and monovalent cations. Biochemistry. May 13, 2008;47(19):5336-53. doi: 10.1021/bi702363u. Epub Apr. 19, 2008.

\* cited by examiner

FIGURE 3

87bp amplicon, RBS60

5'- TGGTAATCTACTGGGACGGAACAGCTTTGAGGTGCGTGTTTGTGCCTGTCCTGGGAGAGACCGGCGCACAGAGGAAGAGAATCTCCGC -3'
                            3'-PO₄- ━━━━━━━━━━ -5' RBS60

3'- ACCATTAGATGACCCTGCCTTGTCGAAACTCCACGCACAAACACGGACAGGACCCTCTCTGGCCGCGTGTCTCCTTCTCTTAGAGGCG -5'

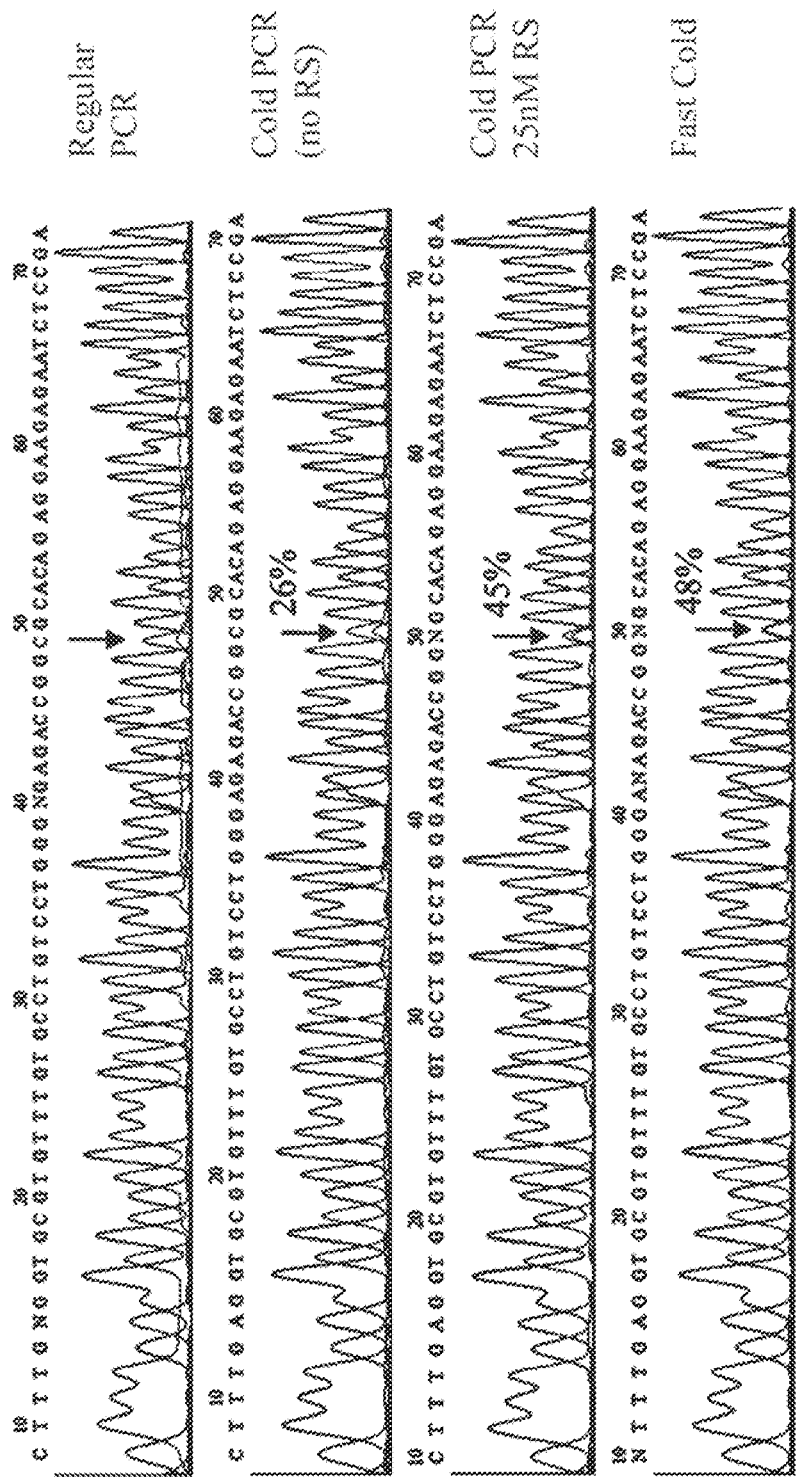

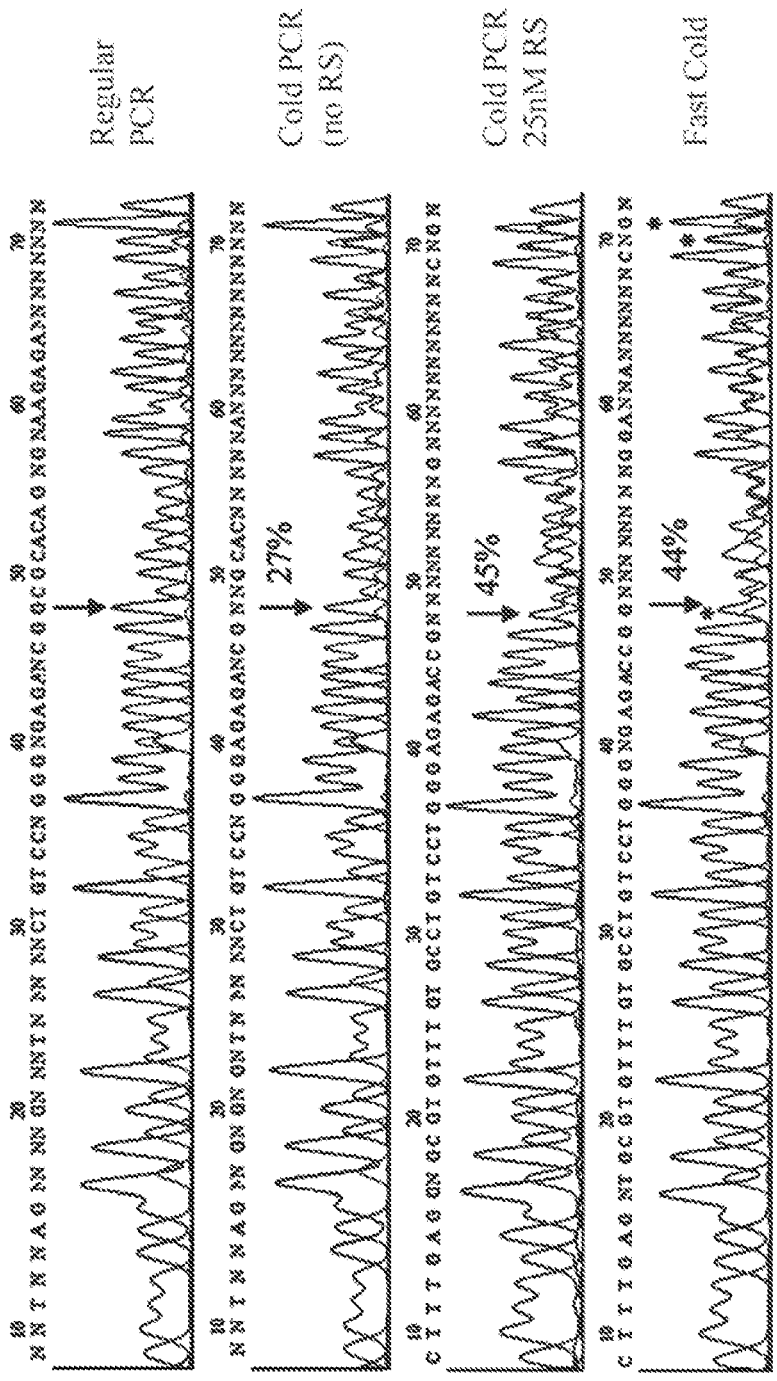

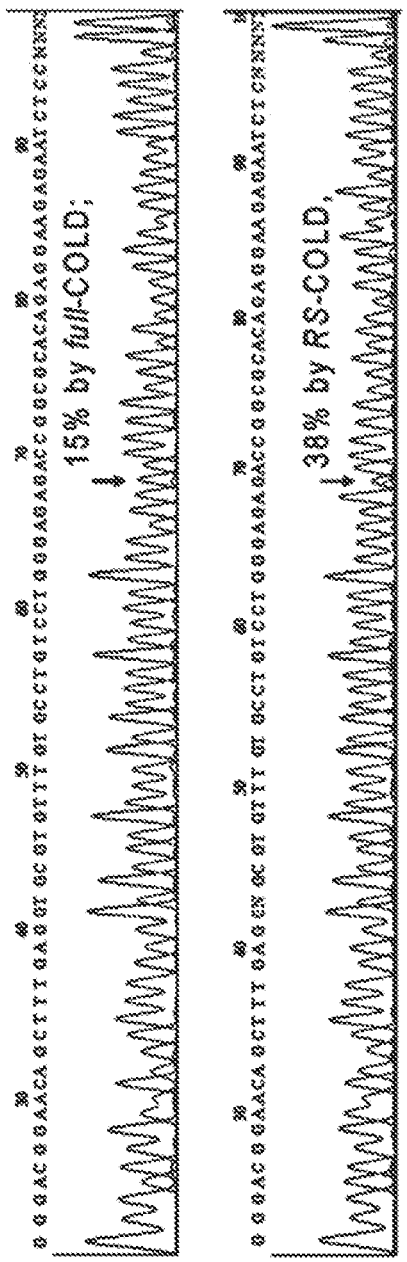

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
gcttctcttt tcctatcctg                                               20

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
cttacctcgc ttagtgct                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
tggtaatcta ctgggacg                                                 18

<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 4
cggagattct cttcctct                                                 18
```

```
<210> SEQ ID NO 5
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 5
tttttttttt tttttttttt tttttttttt tggtaatcta ctgggacg              48

<210> SEQ ID NO 6
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 6
ggacggaaca gcttt                                                   15

<210> SEQ ID NO 7
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 7
ctggccgcgt gtctc                                                   15

<210> SEQ ID NO 8
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 8
ctctgtgcgc cggtctctcc caggacaggc acaaacacgc acctcaaagc tgttccgtcc  60

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gcttctcttt tcctatcctg                                              20

<210> SEQ ID NO 10
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 10
cttacctcgc ttagtgct                                                18

<210> SEQ ID NO 11
<211> LENGTH: 18
<212> TYPE: DNA
<213> ORGANISM: Artificial Sequence
<220> FEATURE:
<223> OTHER INFORMATION: Synthetic Polynucleotide
```

```
<400> SEQUENCE: 11
ttgcttctct tttcctat                                                    18

<210> SEQ ID NO 12
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 12
tttttttttt tttttttttt tttttttttt tttttttttt ttgcttctct tttcctatcc     60

<210> SEQ ID NO 13
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 13
cttcctctgt gcgccggtct ctcccaggac aggcacaaac acgcacctca aagctgttcc     60
gtcccagtag attaccacta ctcaggatag                                       90

<210> SEQ ID NO 14
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 14
tggtaatcta ctgggacgga acagctttga ggtgcgtgtt tgtgcctgtc ctggagaga      60 ccggcgcaca gaggaagaga atctccgc                                        88

<210> SEQ ID NO 15
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 15
gcggagattc tcttcctctg tgcgccggtc tctcccagga caggcacaaa cacgcacctc     60
aaagctgttc cgtcccagta gattacca                                        88

<210> SEQ ID NO 16
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 16
ctttgaggtg cgtgtttgtg cctgtcctgg gagagaccgg cgcacagagg aagagaatct     60
ccga                                                                   64

<210> SEQ ID NO 17
<211> LENGTH: 64
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (18)..(18)
<223> OTHER INFORMATION: n is a, c, g, or t

<400> SEQUENCE: 17
ctttgaggtg cgtgttnntg cctgtcctgg gagagaccgg cgcacagagg aagagaatct    60
ccga                                                                64

<210> SEQ ID NO 18
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 18
ctttgaggng cgtgttnntg cctgtcctgg gagagaccgg cgcacagagg aagagaatct    60
ccga                                                                64

<210> SEQ ID NO 19
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 19
nnntgnggng cgtgtttgng cctgtcctgg gnnagaccgg cgcacagagg aagagaatct    60 ccgn                                                                64

<210> SEQ ID NO 20
<211> LENGTH: 65
<212> TYPE: DNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (18)..(21)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t

<400> SEQUENCE: 20
ntttnagnng ngnnnttnnn nctgtccngn gnnagaccgg cgcacagagg aagagaanct    60 ccgnn                                                               65

<210> SEQ ID NO 21
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
```

```
<222> LOCATION: (18)..(21)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (52)..(55)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 21
nttnnagnng nnngnttnnn nctgncctgn nannnancgg cgcacagagn annnnannct    60 ccgn                                                                64

<210> SEQ ID NO 22
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 22
ctttgaggng cgtgtttnng cctgtcctgg gagagaccgg cgcacagagg aagagaatct    60
ccga                                                                64

<210> SEQ ID NO 23
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
```

<221> NAME/KEY: misc_feature
<222> LOCATION: (18)..(19)
<223> OTHER INFORMATION: n is a, c, g, or t

<400> SEQUENCE: 23
ntttgaggng cgtgttttnng cctgtcctgg gagagaccgg cgcacagagg aagagaatct    60
ccga                                                                 64

<210> SEQ ID NO 24
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t

<400> SEQUENCE: 24
ctttgnggtg cgtgtttgtg cctgtcctgg gngagaccgg cgcacagagg aagagaatct    60
ccga                                                                 64

<210> SEQ ID NO 25
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 25
ctttgaggtg cgtgtttgtg cctgtcctgg gagagaccgg cgcacagagg aagagaatct    60
ccga                                                                 64

<210> SEQ ID NO 26
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: n is a, c, g, or t

<400> SEQUENCE: 26
ctttgaggtg cgtgtttgtg cctgtcctgg gagagaccgg ngcagagagg aagagaatct    60
ccga                                                                 64

<210> SEQ ID NO 27
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

```
<220> FEATURE:
<221> NAME/KEY: misc_feature
<222> LOCATION: (41)..(41)
<223> OTHER INFORMATION: n is a, c, g, or t

<400> SEQUENCE: 27
ntttgaggtg cgtgtttgtg cctgtcctgg ganagaccgg ngcacagagg aagagaatct    60
ccga                                                                 64

<210> SEQ ID NO 28
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (8)..(11)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (57)..(64)
<223> OTHER INFORMATION: n is a, c, g, or t

<400> SEQUENCE: 28
nntnnagnnn ngnnntnnnn nctgtccngg gngagancgg cgcacagngn aagagannnn    60 nnnn                                                                 64

<210> SEQ ID NO 29
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
```

```
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (46)..(50)
<223> OTHER INFORMATION: n is a, c, g, or t
<220> FEATURE:
<221> NAME/KEY: misc_feature
<222> LOCATION: (52)..(64)
<223> OTHER INFORMATION: n is a, c, g, or t

<400> SEQUENCE: 29
nntnnagnng ngngntnnnn nctgtccngg gagagancgn ngcacnnnnn annnnnnnnn    60 nnnn                                                                64

<210> SEQ ID NO 30
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (40)..(48)
<223> OTHER INFORMATION: n is a, c, g, or t
<220> FEATURE:
<221> NAME/KEY: misc_feature
<222> LOCATION: (50)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
```

<400> SEQUENCE: 30
ctttgaggng cgtgtttgtg cctgtcctgg gagagaccgn nnnnnnngn nnnnnnnnn    60 cngn    64

<210> SEQ ID NO 31
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (41)..(48)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 31
ctttgagntg cgtgtttgtg cctgtcctgg gngagaccgg nnnnnnngg annannnnn    60 cngn    64

<210> SEQ ID NO 32
<211> LENGTH: 77
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (75)..(77)
<223> OTHER INFORMATION: n is a, c, g, or t

<400> SEQUENCE: 32
gggacggaac agctttgagg tgcgtgtttg tgcctgtcct gggagagacc ggcgcacaga    60
ggaagagaat ctccnnn    77

<210> SEQ ID NO 33
<211> LENGTH: 77
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(21)
<223> OTHER INFORMATION: n is a, c, g, or t
<220> FEATURE:

```
<221> NAME/KEY: misc_feature
<222> LOCATION: (74)..(77)
<223> OTHER INFORMATION: n is a, c, g, or t

<400> SEQUENCE: 33
gggacggaac agctttgagg ngcgtgtttg tgcctgtcct gggagagacc ggcgcacaga      60
ggaagagaat ctcnnnn                                                     77
```

FULL COLD-PCR ENRICHMENT WITH REFERENCE BLOCKING SEQUENCE

RELATED APPLICATIONS

The present application is a continuation of U.S. application Ser. No. 14/107,291, filed Dec. 16, 2013, which is a continuation of U.S. application Ser. No. 13/042,549, filed Mar. 8, 2011, which claims priority under 35 U.S.C. § 119(e) to U.S. Application No. 61/311,642, filed Mar. 8, 2010, the entire contents of each of which are incorporated herein by reference.

FIELD OF THE INVENTION

The invention pertains to improvements to the amplification and enrichment of low prevalence target sequences, e.g. mutations, in nucleic acid samples. In particular, the invention pertains to the use of reference blocking sequences during full COLD-PCR (CO-amplification at Lower Denaturation temperature).

BACKGROUND OF THE INVENTION

A commonly encountered situation in genetic analysis entails the need to identify a low percent of variant DNA sequences ('target sequences') in the presence of a large excess of non-variant sequences ('reference sequences'). Examples for such situations include: (a) identification and sequencing of a few mutated alleles in the presence of a large excess of normal alleles; (b) identification of a few methylated alleles in the presence of a large excess of unmethylated alleles (or vice versa) in epigenetic analysis; (c) detection of low levels of heteroplasmy in mitochondrial DNA; (d) detection of drug-resistant quasi-species in viral infections and (e) identification of tumor-circulating DNA in blood of cancer patients (where people are suspected of having cancer, to track the success of cancer treatment or to detect relapse) in the presence of a large excess of wild-type alleles.

The inventor of the present application has previously described COLD-PCR methods for enriching the concentration of low abundance alleles in a sample PCR reaction mixture; see published patent PCT application entitled "Enrichment of a Target Sequence", International Application No. PCT/US2008/009248, now U.S. Ser. No. 12/671,295, by Gerassimos Makrigiorgos and assigned to the assignee of the present invention. The described COLD-PCR enrichment methods are based on a modified nucleic acid amplification protocol which incubates the reaction mixture at a critical denaturing temperature "$T_c$". The prior patent application discloses two formats of COLD-PCR, namely full COLD-PCR and fast COLD-PCR.

In full COLD-PCR, the reaction mixture is subjected to a first denaturation temperature (e.g., 94° C.) which is chosen well above the melting temperature for the reference (e.g., wild-type) and target (e.g., mutant) sequences similar to conventional PCR. Then, the mixture is cooled slowly to facilitate the formation of reference-target heteroduplexes by hybridization. Steady lowering of the temperature in a controlled manner from 94° C. to 70° C. over an 8 minute time period is typical to assure proper hybridization. Alternatively, the temperature is rapidly lowered to 70° C. and retained at this temperature for 8 min to assure proper hybridization. Once cooled, the reaction mixture contains not only reference-target heteroduplexes but also reference-reference homoduplexes (and to a lesser extent target-target homoduplexes). When the target sequence and reference sequence cross hybridize, minor sequence differences of one or more single nucleotide mismatches or insertions or deletions anywhere along a short (e.g., <200 bp) double stranded DNA sequence will generate a small but predictable change in the melting temperature ($T_m$) for that sequence (Lipsky, R. H., et al. (2001) Clin Chem, 47, 635-644; Liew, M., et al. (2004) Clin Chem, 50, 1156-1164). Depending on the exact sequence context and position of the mismatch, melting temperature changes of 0.1-20° C., are contemplated. Full COLD-PCR, as described in the above referred patent application, is premised on the difference in melting temperature between the double stranded reference sequence and the hybridized reference-target heteroduplexes. After cooling down to form reference-target heteroduplexes, the reaction mixture is incubated at a critical denaturing temperature ($T_c$), which is chosen to be less than the melting temperature for the double stranded reference sequence and higher than the lower melting temperature of the reference-target heteroduplexes, thereby preferentially denaturing the cross hybridized target-reference heteroduplexes over the reference-reference homoduplexes.

The critical denaturing temperature ($T_c$) is a temperature below which PCR efficiency drops abruptly for the reference nucleic acid sequence (yet sufficient to facilitate denaturation of the reference-target heteroduplexes). For example, a 167 bp p53 sequence amplifies well if the PCR denaturing temperature is set at 87° C., amplifies modestly at 86.5° C. and yields no detectable product if PCR denaturation is set at 86° C. or less. Therefore, in this example $T_c$~86.5° C. After intermediate incubation at the critical denaturing temperature (Tc), the primers are annealed to the denatured target and reference strands from the denatured heteroduplexes and extended by a polymerase, thus enriching the concentration of the target sequence relative to the reference sequence. One of the advantages of full COLD-PCR is that the same primer pair is used for both target and reference sequences.

Fast COLD-PCR, as described in the above referred patent application, is premised on there being a difference in melting temperature between the double stranded reference sequence (e.g., wild-type sequence) and the double stranded target sequence mutant sequence). In particular, the melting temperature of the target sequence must be lower than the reference sequence. The critical denaturing temperature ($T_c$) in fast COLD-PCR is a temperature below which PCR efficiency drops abruptly for the double stranded reference nucleic acid sequence, yet is still sufficient to facilitate denaturation of the double stranded target sequence. During the fast COLD-PCR enrichment cycle, the reaction mixture is not subjected to denaturation at a temperature (e.g., 94° C.) above the melting temperature of the reference sequence as in the first step of the full COLD-PCR cycle. Rather, the reaction mixture is incubated at a critical denaturing temperature (e.g., $T_c$=83.5° C.), which is chosen either (a) to be less than the melting temperature for the double stranded reference sequence and higher than the lower melting temperature of the double stranded target sequence, or; (b) to be lower than the Tm of both reference and target sequences, whilst still creating a differential between the degree of denaturation of reference and target sequences. After incubation at the critical denaturing temperature ($T_c$), the primers are annealed to the denatured target strands and extended by a polymerase, thus enriching the concentration of the target sequence relative to the reference sequence. Again, the same primer pair is used for both target and reference sequences.

Enrichment via full COLD-PCR has been found to be relatively inefficient, and time consuming, compared to enrichment via fast COLD-PCR. However, the use of fast COLD-PCR is limited to applications in which the melting temperature of the double stranded target sequence is suitably less than the melting temperature for the double stranded reference sequence. For example, mutations will not be detectable in sequencing data for a sample with a low abundance of mutant sequences that has been subjected to fast COLD-PCR if the melting temperature of the mutant sequence is the same or higher than the melting temperature of the wild-type sequence. Therefore, it is desired to improve the efficacy and rate of the full COLD-PCR cycle.

It is believed that the relative inefficiency of full COLD-PCR is due primarily to the paucity of heteroduplexes formed particularly during the early cycles of full COLD-PCR. Even if slow cool down during the hybridization step is optimized (e.g., steadily cool down for 8 minutes from 94° C. to 70° C.), the very low concentration of target (e.g. mutant) strands especially during early cycles reduces the ability to form heteroduplexes. Increasing the time for hybridization cool down is not desired, and in any event has not been found to be particularly effective to improve enrichment. Another reason that full COLD-PCR may be relatively less efficient than fast COLD-PCR is that the amplicons during later cycles of full COLD-PCR have a propensity to reform their homoduplexes rather than form heteroduplexes.

One object of the present invention is to improve the efficiency of heteroduplex formation in the early cycles of full COLD-PCR. Another object is to decrease the overall cycle time for full COLD-PCR.

SUMMARY OF THE INVENTION

The present invention is directed to methods for enriching low abundance alleles in a sample, and is directed in particular to the use of an excess amount of reference blocking sequence in the reaction mixture in order to improve the efficiency, and reduce cycle time, of full COLD-PCR.

The present invention involves a modification to the COLD-PCR methods described in connection with FIGS. 1 and 2 of the above referred patent application, "Enrichment of a Target Sequence", International Application No. PCT/US2008/009248, now U.S. Ser. No. 12/671,295, by Gerassimos Makrigiorgos and assigned to the assignee of the present invention, and which is hereby incorporated herein by reference. More specifically, in accordance with the invention, an engineered reference blocking sequence (e.g., a single stranded oligonucleotide) is added in excess to the reaction mixture prior to subjecting the reaction mixture to thermocycling per a modified, full COLD-PCR protocol.

The modified, full COLD-PCR method involves the preparation of an amplification reaction mixture containing a nucleic acid sample. The nucleic acid sample will have a reference sequence, such as a wild-type sequence, and will also be suspected of containing one or more target sequences, such as one or more mutant sequences. As mentioned, the purpose of the invention is to enrich the concentration of the target sequence, and therefore in most circumstances, the method will be used when the target sequence, if present, is in low abundance. The target sequence in accordance with the invention is at least 50% homologous to the reference sequence, although the method is especially well suited to enrich a mutant allele containing about 1 to 10 nucleotide sequence changes. The target sequence is amplifiable via PCR with the same pair of primers as those used for the reference sequence. As mentioned, the invention involves the presence of a reference blocking sequence in the reaction mixture at an excess concentration level. The reference blocking sequence is a nucleic acid sequence complementary with at least a portion of one of the strands of the reference sequence between its primer sites, or partly overlapping the primer sites. The reference blocking sequence added to the reaction mixture is desirably single stranded (but can also be double stranded inasmuch as the initial denaturing step will result in denatured, single stranded reference blocking sequences).

In accordance with the full COLD-PCR protocol, the reaction mixture is subjected to a first denaturing temperature, e.g. 95° C., which is above the melting temperature ($T_m$) of the reference sequence and also the target sequence, and results in denatured strands of the reference sequence and the target sequence. The reaction mixture is cooled to promote hybridization, for example to about 70° C. Since the cooling down occurs in the presence of an excess amount of reference blocking sequences, the reference blocking sequences preferentially hybridize with the complementary strand of the reference sequence, and also the complementary strand of the target sequence. For example assuming that single stranded reference blocking sequence is added in excess at the beginning of the process, the reaction mixture at this point in the process will contains heteroduplexes of the reference blocking sequences and the complementary reference (e.g., wild-type) strand and heteroduplexes of the reference blocking sequences and the target (e.g. mutant) strands. The reaction mixture at this point also contains the denatured negative strands for the reference and target sequences. The formed heteroduplexes present in the modified full COLD-PCR cycle are fundamentally different from the reference-target heteroduplexes formed in the full COLD-PCR protocol described in the above referenced patent application. Supplying an excess amount of reference blocking sequence promotes faster hybridization (e.g., about 30 seconds) than in the prior full COLD-PCR protocol (e.g., about minutes). In a preferred embodiment of the present invention, the cool down hybridization step is less than one minute in duration.

The reaction mixture is then subjected to a critical temperature (e.g., $T_c$=84.5° C.) which is sufficient to permit preferential denaturation of the target strands from the reference blocking sequence. The critical temperature ($T_c$) is selected so that duplexes of the reference blocking strands and the complementary reference strands remain substantially undenatured when the reaction mixture is incubated at $T_c$ yet duplexes of the reference blocking strands and the target strands substantially denature. The term "substantially" means at least 60%, and preferably at least 90% or more preferably at least 98% in a given denatured or undenatured form. The melting temperature for the duplex of the reference blocking sequence and the target strands will always be less than the melting temperature of the duplex of the reference blocking sequence and the complementary reference strand because the former contains a mismatch whereas the latter does not.

After preferential denaturation, the temperature of the reaction mixture is reduced so as to permit the primer pairs to anneal to the free target and reference strands in the reaction mixture. Again, assuming that single stranded reference blocking oligonucleotides are added in excess at the beginning of the process, at this point in the cycle there are, theoretically, two free strands of the target sequence compared to the initial denaturation step and only one free reference strand. The other reference strand is hybridized with the reference blocking sequence, and is therefore unavailable for amplification. The annealed primers are then extended, thus resulting in exponential amplification of the target sequence, while the reference strand is only amplified linearly. Accordingly, the target sequence is gradually enriched relative to the reference sequence in the sample during the COLD-PCR cycles.

The method is likely repeated ten to thirty cycles or more. It has been found to substantially increase enrichment of target amplicons and decrease cycle time for full COLD-PCR. It is also able to enrich homozygous mutations, which would not form heteroduplexes in the prior full COLD-PCR protocol.

The length of the reference blocking sequence can be equal to, or smaller or larger than the length of the target or reference sequences. In a preferred embodiment, the reference blocking sequence is several bases smaller than the target and reference sequences, on each side of the sequence so that the primers do not bind appreciably to the reference sequence. Hence, the reference blocking sequence cannot be extended by the primers that amplify the target sequence. To this end, optionally the 3' OH end of the reference blocking sequence can be blocked to DNA-polymerase extension. Also, optionally, the 5'-end of the reference blocking sequence may be designed with nucleotide sequence that partially overlaps the primer binding sites such that 5' to 3' exonucleolysis by Taq DNA polymerases (i.e. degradation of the hybridized reference blocking sequence) may be prevented.

As mentioned, the reference sequence is single stranded or double stranded. In a preferred embodiment, the reference blocking sequence is single stranded nucleic acid. However, the reference blocking sequence can take other forms, such as a chimera between single stranded DNA, RNA, peptide nucleic acid (PNA) or locked nucleic acid (LNA), or another modified nucleotide. The PNA or LNA positions on the chimera sequence can be selected to match positions where mutations are likely, so as to maximize the effect of potential mismatches at those positions. The reference blocking sequence can be also single stranded PNA or single stranded DNA.

Other embodiments and advantages of the invention may be apparent to those skilled in the art upon reviewing the drawings and the following detailed description.

BRIEF DESCRIPTION OF THE DRAWINGS

FIG. 3 is a schematic drawing illustrating a 60 bp reference blocking sequence for implementing one embodiment of the invention. An 87 bp amplicon is preliminarily amplified using the underlined primers. A complementary reference blocking sequence is designed for each strand and contains a 3' non-extensible phosphate group. (SEQ ID NOs: 14 and 15)

FIG. 6 displays Sanger sequencing data for the enrichment of HCC2218 mutant alleles from samples processed using regular PCR (SEQ ID NO:24), full COLD PCR without the use of a reference blocking sequence in the reaction mixture (SEQ ID NO:25); full COLD-PCR with an excess of reference blocking sequence (RS) in the reaction mixture (SEQ ID NO:26), and fast COLD-PCR (SEQ ID NO:27), respectively.

FIG. 7 displays Sanger sequencing data for the enrichment of TL92 mutant alleles (1 bp G del) from samples processed using regular PCR (SEQ ID NO:28), full COLD PCR without the use of a reference blocking sequence in the reaction mixture (SEQ ID NO:29); full COLD-PCR with an excess of reference blocking sequence (RS) in the reaction mixture (SEQ ID NO:30), and fast COLD-PCR (SEQ ID NO:31), respectively.

FIG. 8 displays Sanger sequencing data for the enrichment of HCC1008 mutant alleles from samples processed using full COLD-PCR with the use of a 90 bp reference blocking sequence (RS) (SEQ ID NOs:32 and 33).

DETAILED DESCRIPTION

Definitions

Figure 1:
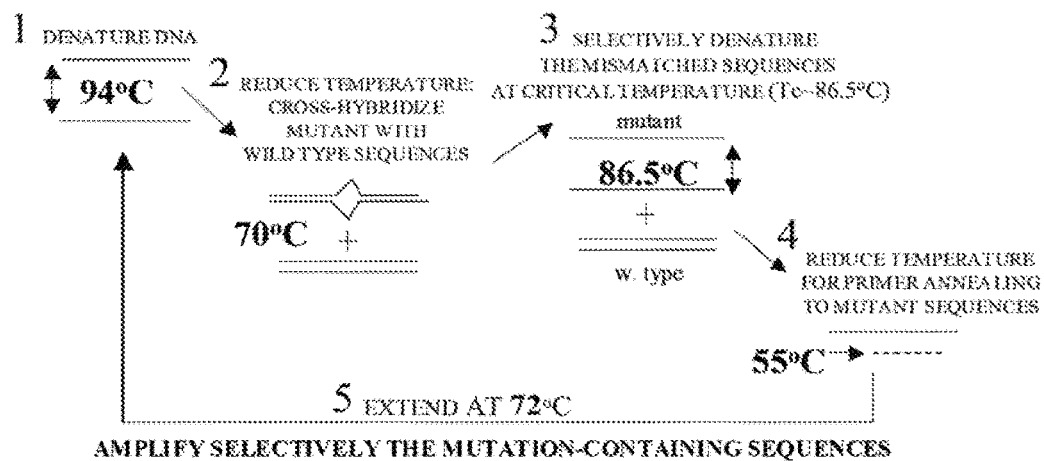
FIG. 1 illustrates a prior art embodiment of full COLD-PCR for selectively enriching a target sequence as described in the prior patent application entitled "Enrichment of a Target Sequence", International Application No. PCT/US2008/009248, now U.S. Ser. No. 12/671,295, and incorporated herein by reference.

As used herein, the term "enriching a target sequence" refers to increasing the amount of a target sequence and increasing the ratio of target sequence relative to the corresponding reference sequence in a sample. For example, where the ratio of target sequence to reference sequence is initially 5% to in a sample, the target sequence may be preferentially amplified in an amplification reaction so as to produce a ratio of 70% target sequence to 30% reference sequence. Thus, there is a 14-fold enrichment of the target sequence relative to the reference sequence.

As used herein the term "target sequence" refers to a nucleic acid that is less prevalent in a nucleic acid sample than a corresponding reference sequence. The target sequence makes-up less than 50% of the total amount of reference sequence+target sequence in a sample. The target sequence may be a mutant allele. For example, a sample (e.g., blood sample) may contain numerous normal cells and few cancerous cells. The normal cells contain non-mutant or wild-type alleles, while the small number of cancerous cells contains somatic mutations. In this case the mutant is the target sequence while the wild-type sequence is the reference sequence.

As used herein, a "target strand" refers to a single nucleic acid strand of a target sequence.

The target sequence must be at least 50% homologous to the corresponding reference sequence, but must differ by at least one nucleotide from the reference sequence. Target sequences are amplifiable via PCR with the same pair of primers as those used for the reference sequence.

As used herein, the term "reference sequence" refers to a nucleic acid that is more prevalent in a nucleic acid sample than a corresponding target sequence. The reference sequence makes-up over 50% of the total reference sequence+target sequence in a sample. Preferably the reference sequence is expressed at the RNA and/or DNA level 10×, 15×, 20×, 25×, 30×, 35×, 40×, 45×, 50×, 60×, 70×, 80×, 90× 100×, 150×, 200× or more than the target sequence. As used herein, a "reference strand" refers to a single nucleic acid strand of a reference sequence.

As used herein, the term "wild-type" refers to the most common polynucleotide sequence or allele for a certain gene in a population. Generally, the wild-type allele will be obtained from normal cells.

As used herein, the term "mutant" refers to a nucleotide change (i.e., a single or multiple nucleotide substitution, deletion, or insertion) in a nucleic acid sequence. A nucleic acid which bears a mutation has a nucleic acid sequence (mutant allele) that is different in sequence from that of the corresponding wild-type polynucleotide sequence. The invention is broadly concerned with somatic mutations and polymorphisms. The methods of the invention are especially useful in selectively enriching a mutant allele which contains between about 1 and 10 nucleotide sequence changes, although is useful even with a higher number of sequence changes. A mutant allele will typically be obtained from diseased tissues or cells and is associated with a disease state.

As used herein the term "melting temperature" or "$T_m$" refers to the temperature at which a polynucleotide dissociates from its complementary sequence. Generally, the $T_m$ may be defined as the temperature at which one-half of the Watson-Crick base pairs in a double stranded nucleic acid molecule are broken or dissociated (i.e., are "melted") while the other half of the Watson-Crick base pairs remain intact in a double stranded conformation. In other words the $T_m$ is defined as the temperature at which 50% of the nucleotides of two complementary sequences are annealed (double strands) and 50% of the nucleotides are denatured (single strands). $T_m$ therefore defines a midpoint in the transition from double-stranded to single-stranded nucleic acid molecules (or, conversely, in the transition from single-stranded to double-stranded nucleic acid molecules).

The $T_m$ can be estimated by a number of methods, for example by a nearest-neighbor calculation as per Wetmur 1991 (Wetmur, J. G. 1991. DNA probes: applications of the principles of nucleic acid hybridization. Crit Rev Biochem Mol Biol 26: 227-259), and by commercial programs including Oligo™ Primer Design and programs available on the internet. Alternatively, the Tm can be determined though actual experimentation. For example, double-stranded DNA binding or intercalating dyes, such as Ethidium bromide or SYBR-green (Molecular Probes) can be used in a melting curve assay to determine the actual $T_m$ of the nucleic acid. Additional methods for determining the $T_m$ of a nucleic acid are well known in the art. Some of these methods are listed in the inventor's prior patent application entitled "Enrichment of a Target Sequence", International Application No. PCT/US2008/009248, now U.S. Ser. No. 12/671,295, by reference herein.

As used herein, "reference blocking sequence" is an engineered single stranded or double stranded nucleic acid sequence, such as an oligonucleotide and preferably has a length smaller than the target sequence. In a preferred embodiment, the reference blocking sequence is several bases smaller than the reference sequence, on each side of the sequence so that the primers do not bind appreciably to the reference sequence. Optionally, the 3' OH end of the reference blocking sequence is blocked to DNA-polymerase extension, the 5-end is modified to prevent 5' to 3' exonucleolysis by Taq DNA polymerases. The reference blocking sequence can also take other forms which remain annealed to the reference sequence when the reaction mixture is subject to the critical temperature "$T_c$", such as a chimera between single stranded DNA, RNA, peptide nucleic acid (PNA or locked nucleic acid (LNA), or another modified nucleotide.

As used in connection with the present invention, the term "critical temperature" or "$T_c$" refers to a temperature selected to preferentially denature duplexes of target strands and the reference blocking sequence. The critical temperature ($T_c$) is selected so that duplexes consisting of the reference blocking strands and complementary reference strands remain substantially undenatured when the reaction mixture is incubated at $T_c$ yet duplexes consisting of the reference blocking strands and the target strands substantially denature. The term "substantially" means at least 60%, and preferably at least 90% or more preferably at least 98% in a given denatured or undenatured form. In the examples provided below, the selected critical temperature "$T_c$" for the intermediate incubation step is 84.5° C., whereas the first denaturing temperature is 95° C.

As used herein, "primer pair" refers to two primers that anneal to opposite strands of a target and reference sequence so as to form an amplification product during a PCR reaction. The target and the reference sequence should be at least 25 bases in order to facilitate primer attachment. The primer pair is designed so as to have a $T_m$ lower than the $T_c$ of the reaction.

As used herein, "homology" refers to the subunit sequence similarity between two polymeric molecules, e.g., two polynucleotides or two polypeptides. An example of an algorithm that is suitable for determining percent sequence identity and sequence similarity are the BLAST and BLAST 2.0 algorithms, which are described in Altschul et al., Nucleic Acids Res. 25:3389-3402 (1997) and Altschul et al., J. Mol. Biol. 215:403-410 (1990), respectively. Software for performing. BLAST analyses is publicly available through the National Center for Biotechnology Information at www.ncbi.nlm.nih.gov/.

Nucleic Acid Amplification Generally

In one embodiment, a nucleic acid sample utilized in the method of the invention comprises genomic DNA having a target and reference sequence. In another embodiment, the nucleic acid sample of the method of the invention comprises target and reference sequences that were previously amplified in a nucleic acid amplification reaction. The skilled artisan will appreciate that there are many methods available to amplify a nucleic acid. Perhaps the most popular method is the polymerase chain reaction (PCR; for example, see, U.S. Pat. Nos. 4,683,195 and 4,683,202, as well as Saiki et al., Science 230:1350-1354 (1985) and Gyllensten et al., PNAS (USA) 85:7652-7656 (1985)). A preferred variation of the PCR method is asymmetrical PCR (for example, see Mao et al., Biotechniques 27(4):674-678 (1999); Lehbein et al., Electrophoresis 19(8-9):1381-1384 (1998); Lazaro et al., Mol. Cell. Probes 6(5):357-359 (1992); and U.S. Pat. No. 6,197,499). Other amplification methods include, but are not limited to, strand displacement amplification (SDA) (see, Walker et al., Nucleic Acids Res. 20(7):1691-1696 (1992), as well as U.S. Pat. Nos. 5,744,311, 5,648,211 and 5,631, 147), rolling circle amplification (RCA) (see PCT publication WO 97/19193), nucleic acid sequence-based amplification (NASBA) (see Compton, Nature 350:91-92 (1991);

as well as U.S. Pat. Nos. 5,409,818 and 5,554,527), transcript mediated amplification (TMA) (see Kwoh et al., PNAS (USA) 86:1173-1177 (1989), as well as U.S. Pat. No. 5,399,491), self sustained sequence replication (3SR) (see Guatelli et al., PNAS (USA) 87:1874-1879 (1990) and ligase chain reaction (LCA) (see U.S. Pat. Nos. 5,427,930 and 5,792,607).

In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of 109 relative to other sequences in genomic DNA. The PCR method is also described in Saiki et al., 1985, Science 230:1350.

PCR is performed using template DNA (target and reference sequences) (at least 1 fg; more usefully, 1-1000 ng) and at least 25 pmol of oligonucleotide primers. A typical reaction mixture includes: 2 μl of DNA, 25 pmol of oligonucleotide primer, 2.5 μl of a suitable buffer, 0.4 μl of 1.25 μM dNTP, 2.5 units of Taq DNA polymerase (Stratagene) and deionized water to a total volume of 25 μl. PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

PCR utilizes a nucleic acid polymerase, or enzyme that catalyzes the polymerization of nucleoside triphosphates. Generally, the enzyme will initiate synthesis at the 3'-end of the primer annealed to the target sequence, and will proceed in the 5'-direction along the template. Known DNA polymerases include, for example, E. coli DNA polymerase 1, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase. The term "nucleic acid polymerase" also encompasses RNA polymerases. If the nucleic acid template is RNA, then "nucleic acid polymerase" refers to an RNA-dependent polymerization activity, such as a reverse transcriptase.

The enrichment procedures of the present invention are performed in a PCR device such as a thermocycler, or more preferably under real-time reaction conditions in a real-time PCR device. Real-time reaction conditions further utilize a nucleic acid detection agent (e.g., dye or probe) in order to measure/detect the PCR product as it is produced.

Samples

As used herein, "sample" refers to any substance containing or presumed to contain a nucleic acid of interest (target and reference sequences) or which is itself a nucleic acid containing or presumed to contain a target nucleic acid of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

Nucleic acid sequences of the invention can be amplified from genomic DNA. Genomic DNA can be isolated from tissues or cells according to the following method. Alternatively nucleic acids sequences of the invention can be isolated from blood by methods well known in the art.

To facilitate detection of a variant form of a gene from a particular tissue, the tissue is isolated. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5 M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 μg/ml DNase-free RNase, and repeating the extraction and ethanol precipitation steps. The yield of genomic DNA, according to this method is expected to be approximately 2 mg DNA/1 g cells or tissue Ausubel et al., supra). Genomic DNA isolated according to this method can be used according to the invention.

The target DNA may also be extracted from whole blood. For example, blood may be drawn by standard methods into a collection tube, preferably comprising siliconized glass, either without anticoagulant for preparation of serum, or with EDTA, sodium citrate, heparin, or similar anticoagulants, most preferably EDTA, for preparation of plasma. The preferred method, although not absolutely required, is that plasma or serum be fractionated from whole blood. Plasma or serum may be fractionated from whole blood by centrifugation, preferably gentle centrifugation at 300 to 800×g for 5-10 minutes, or fractionated by other standard methods. Since heparin may interfere with PCR, use of heparinized blood may require pretreatment with heparinase. Thus, EDTA is the preferred anticoagulant for blood specimens. Either freshly-collected blood plasma or serum, or frozen (stored) and subsequently thawed plasma or serum can be used in the methods of the invention. Stored plasma or serum should be kept at −20° C. to −70° C., and freshly-collected plasma or serum kept refrigerated or maintained on ice until use. The DNA may then be extracted by methods well known in the art.

The method of the present invention can be used to detect whether methylation has occurred in a target sequence. The methylation detection method comprises a chemical or enzymatic approach for methylation-sensitive treatment of DNA. Chemical treatments include the incubation of DNA with sodium bisulfite, which selectively converts non-methylated cytosines to uracils. The DNA is first heat-denatured and then treated with 5M bisulfite, pH 5-7. Pretreatment of genomic DNA to remove pre-existing uracils is used prior to bisulfite treatment. This pretreatment consists of uracil glycosylase treatment in the presence of 5 mM hydroxylamine, pH 7.

Because the methylated cytosines of the target sequence are converted to uracils, they will now form mismatches when duplexed with the reference blocking sequence in the hybridization cool down step of full COLD-PCR (in the presence of reference blocking sequence).

Full COLD-PCR in the Absence of Reference Blocking Sequence (Prior Art)

FIG. 1 illustrates the prior art procedure known as full COLD-PCR for enriching a target sequence in a nucleic acid sample containing a target and reference sequence, as explained the above incorporated U.S. application Ser. No. 12/671,295, entitled "Enrichment of a target Sequence". FIG. 1 is a reproduction of FIG. 1 in the above incorporated patent application.

The target and reference sequences can be obtained from a variety of sources including, genomic DNA, cDNA, viral DNA, mammalian DNA, fetal DNA or bacterial DNA. While the reference sequence is generally the wild-type allele and the target sequence is the mutant allele, the reverse may also be true. The mutant allele may include any one or more nucleotide deletions, insertions or alterations. In some embodiments, the mutant allele is a somatic mutation. In other embodiments, the target sequence is methylated DNA while the reference sequence is un-methylated DNA.

The method includes subjecting the amplification reaction mixture to a first denaturing temperature (FIG. 1A, Step 1) that is above the melting temperature "$T_m$" of a reference sequence. The $T_m$ of a nucleic acid can be determined through experimentation or estimated by calculation. The skilled artisan is well aware of numerous well known methods for determining the $T_m$ of a nucleic acid some of which are described herein. The first denaturing temperature is generally selected as one would generally select the denaturing temperature of a PCR reaction and should be sufficiently high so as to allow the full denaturing of the target and reference sequences (e.g., 94° C.). In one embodiment, the first denaturing temperature is about 1° C. to 30° C. above the $T_m$ of the reference sequence, more preferably the $T_m$ of the reference sequence is about 5° C. to 20° C. above the $T_m$ of the reference sequence.

Next, the temperature of the amplification reaction mixture is decreased allowing the target sequences and reference sequences to hybridize (FIG. 1A, Step 2). This annealing step results in the formation of duplexes of target-target, reference-reference and target-reference sequences, but should be optimized to form target-reference duplexes. The PCR primers used in the method are designed to have a melting temperature that prevents them from binding to the target and reference sequences at this intermediate temperature. As mentioned above, the requirement of target-reference hybridization and the relatively large amount of time needed for cool down (FIG. 1A, Step 2) has been found to limit the effectiveness of full COLD-PCR at least in some applications.

The target-reference hybridization duplexes are then preferentially denatured by increasing the temperature of the reaction mixture to the $T_c$ (FIG. 1A, Step 3). The $T_c$ or critical temperature in FIG. 1 is selected to be below the $T_m$ of the reference sequence yet above the $T_m$ of the target-reference duplex. As mentioned previously, when the target sequence and reference sequence cross hybridize, minor sequence differences of one or more single nucleotide mismatch anywhere along a double stranded DNA sequence will generate a small but predictable change in the melting temperature ($T_m$) for that sequence (Lipsky, R. H., et al. (2001) *Clin Chem*, 47, 635-644; Liew, M., et al. (2004) *Clin Chem*, 50, 1156-1164). Depending on the exact sequence context and position of the mismatch, melting temperature changes in the range of 0.1-20° C. are possible. The $T_c$ is generally applied (FIG. 1A, Step 3) from about 1 second to 5 minutes, more preferably 5 seconds to 30 seconds. It is possible to oscillate between steps 3 and 2 for multiple cycles if desired.

After the preferential denaturing of the target-reference hybridization duplexes, the temperature of the reaction mixture is reduced so as to allow one or more primers to anneal to the target sequence (FIG. 1A, Step 4). The annealed primers are then extended by a nucleic acid polymerase (FIG. 1A, Step 5), thus enriching the target sequence in the population of nucleic acids contained in the sample.

The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device, such as the SMARTCYCLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a probe operatively coupled to a fluorescent dye) for quantifying and/or monitoring the amplification products of the reaction. Once the enrichment of the target sequence is complete the sample may be further processed, e.g., subjected to a sequencing reaction. The enriched alleles may be further processed by a variety of procedures including: MALDI-TOF, HR-Melting, Di-deoxy-sequencing, Single-molecule sequencing, second generation high throughput sequencing, pyrosequencing, RFLP, digital PCR and quantitative-PCR (See FIG. 1B). A more detail description of these processing technologies as well as diagnostic assays is included in the above mentioned U.S. application Ser. No. 12/671,295, entitled "Enrichment of a target Sequence", and incorporated herein by reference.

Full COLD-PCR Cycle with Excess Reference Blocking Sequence in Reaction Mixture

Figure 2:
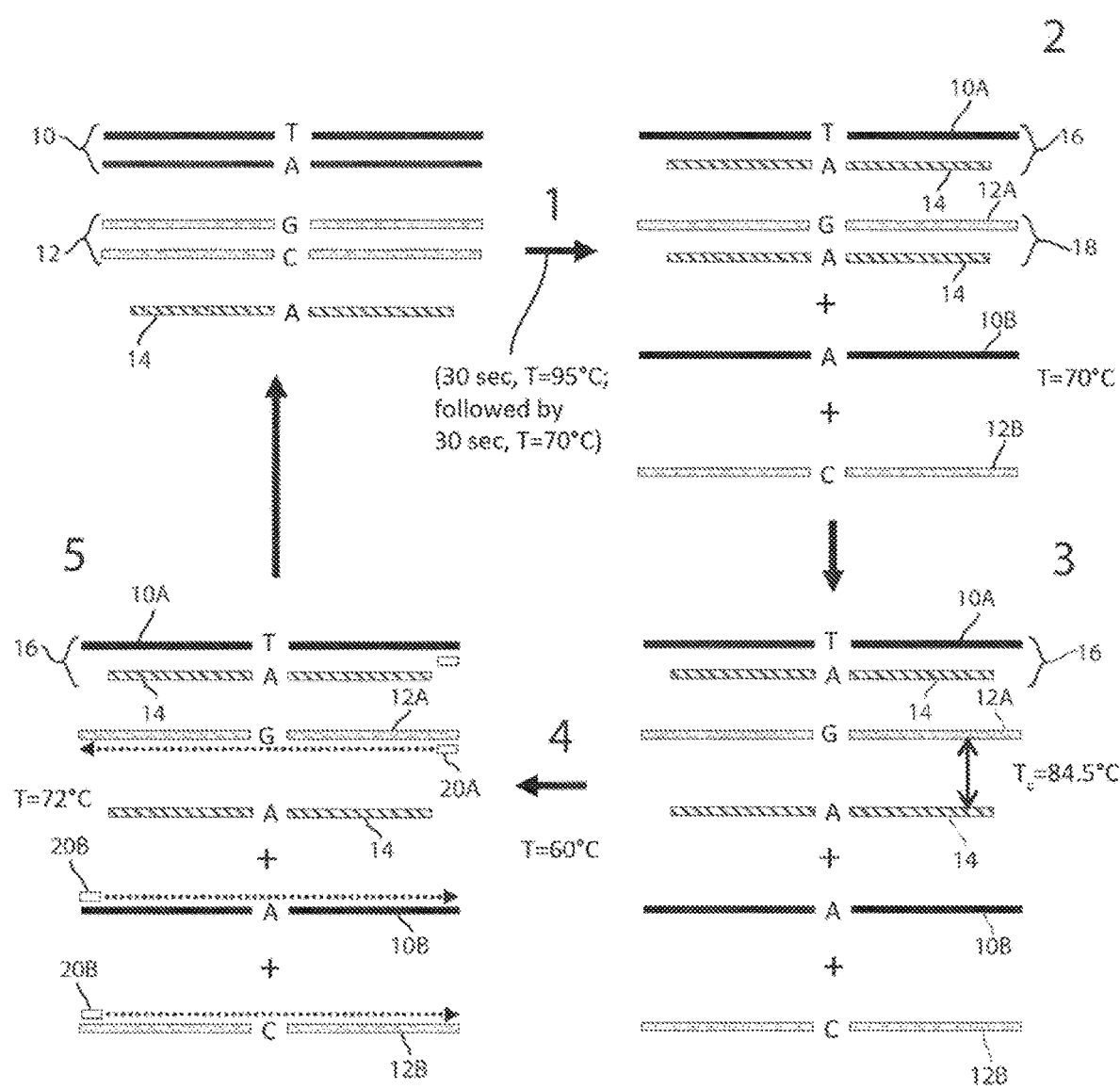
FIG. 2 illustrates the principle of the present invention which improves full COLD-PCR via the presence of an excess amount of a reference blocking sequence in the amplification reaction mixture.

FIG. 2 illustrates enrichment of a target sequence in accordance with the modified full COLD-PCR method of the present invention. To begin (FIG. 2, step 1), the nucleic acid sample contains a double-stranded reference sequence 10 (e.g., a wild-type sequence) and contains a double-stranded target sequence 12 (e.g., a mutant sequence). The amplification reaction mixture contains the sample, other PCR ingredients, and in accordance with the invention a reference blocking sequence 14 at an excess concentration level, such as 25 nM. In FIG. 2, the depicted reference blocking sequence 14 is a single-stranded nucleic acid sequence complementary with one of the strands 10A of the reference sequence 10 between its primer sites.

The reaction mixture in step 1 of FIG. 2 is subjected to a first denaturing temperature, e.g. 95° C. for 10 seconds, which results in denatured strands of the reference sequence 10A, 10B and the target sequence 12A, 12B. The reaction mixture is then cooled to promote hybridization, 70° C. for 30 seconds, which is a dramatic reduction from the normal 8 minute cool down in the prior art. Since the cool down occurs in the presence of an excess amount of reference blocking sequences 14, the reference blocking sequences 14 preferentially hybridize with the complementary strand 10A of the reference sequence and also the complementary strand 12A of the target sequence. Step 2 in FIG. 2 illustrates the state of the reaction mixture after the hybridization cool down to 70° C. in addition to heteroduplexes 16 of the reference blocking sequence 14 and the complementary reference strand 10A and heteroduplexes 18 of the reference blocking sequence 14 and the complementary target strand 12A, the reaction mixture also contains the denatured negative strands 10B and 12B of the reference and target sequences, respectively.

In step 3 of FIG. 2, the reaction mixture is then subjected to the critical temperature "$T_c$", e.g., 84.5° C., which is chosen to permit preferential denaturation of the heteroduplexes 18 of the target strand 12A and reference blocking sequence 14. The critical temperature ($T_c$) is selected so that duplexes 16 of the reference blocking strands 14 and the complementary reference strands 10A remain substantially undenatured when the reaction mixture is incubated at "$T_c$". The melting temperature for the duplex 18 of the reference blocking sequence 14 and the target strand 10B will always be less than the melting temperature of the duplex 16 of the reference blocking sequence 14 and the complementary reference strand 10A because the reference blocking sequence 14 is fully complementary with at least a portion of the reference strand 10A, and there will be at least one mismatch with the target strand 12A.

Referring to step 4 of FIG. 2, after preferential denaturation, the temperature of the reaction mixture is reduced, e.g., 60° C., to permit the primer pair 20A, 20B to anneal to the free target strands 12A, 12B and the free reference strand 10B in the reaction mixture. Reference number 20A refers to the forward primer and reference number 20B refers to the reverse primer. As described previously, the target sequence 12 is amplifiable via the same pair of primers 20A, 20B as those used for the reference sequence 10. Step 5 of FIG. 2 illustrates two free strands 12A, 12B of the target sequence compared to the initial denaturation step and only one free reference strand 10B. The other reference strand 10A is hybridized with the reference blocking sequence 14, and is therefore unavailable for amplification. The temperature of the reaction mixture is then raised, e.g. 72° C., to extend the annealed primers 20A, 20B, thus enriching the concentration of the target sequence 12 in the reaction mixture relative to the reference sequence 10. The method is likely repeated five to thirty cycles.

The method illustrated in FIG. 2 can and should be optimized for individual protocols. Such protocols can be embodied in software, if desired, for operating various PCR and real-time PCR equipment.

Design Considerations for the Preferred Reference Blocking Sequence

As mentioned, the reference blocking sequence can take many forms, yet the preferred form is single stranded, non-extensible DNA. More specifically, the preferred reference blocking sequence has the following characteristics:

(a) comprises single-stranded DNA of up to 200 bp in length;

(b) has a length that is several bases smaller than the target sequence (e.g. 8-12 bases on each side of the sequence) so that the primers do not bind appreciably to the reference sequence when annealed to the reference blocking sequence; and also do not bind appreciably to the reference blocking sequence itself; and (c) contains a 3'-end that is blocked to DNA-polymerase extension.

Such a reference blocking sequence can be synthesized in one of the several methods. First, the reference blocking sequence can be made by direct synthesis using standard oligonucleotide synthesis methods that allow modification of the 3'-end of the sequence. The 3'-end may contain a phosphate group, an amino-group, a di-deoxy-nucleotide or any other moiety that blocks 5' to 3' polymerase extension. Alternatively, the reference blocking sequence can be made by polymerase synthesis during a PCR reaction that generates single stranded DNA as the end product. In this case, the generated single stranded DNA corresponds to the exact sequence necessary for the reference blocking sequence. Methods to synthesize single stranded. DNA via polymerase synthesis are several and well known to those skilled in the art. For example, asymmetric PCR or LATE PCR would be suitable. Alternatively, a single stranded DNA reference blocking sequence can be synthesized by binding double stranded PCR product on solid support. This is accomplished by performing a standard PCR reaction, using a primer pair one of which is biotinylated. Following PCR, the PCR product is incubated with a streptavidin-coated solid support (e.g. magnetic heads) and allowed to bind to the beads. Subsequently, the temperature is raised to 95° C. for 2-3 minutes to denature DNA and release to the solution the non-biotinylated DNA strand from the immobilized PCR product. The magnetic beads with the complementary DNA strand are then removed and the single stranded product remaining in the solution serves as the reference blocking sequence.

Before the single stranded reference blocking sequence is used, the 3'-end is preferably blocked to polymerase extension. This can be accomplished in several ways well known to those skilled in the art. For example, a reaction with Terminal Deoxynucleotide Transferase (TdT) can be employed, in the presence of di-deoxy-nucleotides (ddNTP) in the solution, to add a single ddNTP to the end of the single stranded reference blocking sequence. ddNTPs serve to block polymerase extension. Alternatively, an oligonucleotide template complementary to the 3'-end of the reference blocking sequence can be used to provide a transient double stranded structure. Then, polymerase can be used to insert a single ddNTP at the 3'-end of the reference blocking sequence opposite the hybridized oligonucleotide.

In another method to synthesize the reference blocking sequence in a double stranded form, a conventional PCR is carried out to amplify a wild type version of the sequence of interest, using primers that contain rare enzymatic restriction sites. Following PCR amplification, restriction enzymes are applied to digest both ends of the PCR product and create overhangs. These overhangs are then subjected to polymerase extension in the presence of di-deoxy-nucleotides, thereby blocking the 3'-end on both sides from further extension. The double-stranded, 3'-end blocked PCR product can then serve as a double stranded reference blocking sequence.

Specific Examples of
Oligonucleotide-Synthesis-Generated Reference
Blocking Sequences Two reference blocking sequences were synthesized: a 60 bp (RBS60) and a 90 bp (RBS90) reference blocking sequence corresponding to sections of p53 exon 8. Table 1 contains the listed sequences for the synthesized RBS60 and RBS90 reference blocking sequences. Both the RBS60 and the RBS90 sequence were synthesized with a 3'-blocking phosphate group by Integrated DNA Technologies, Inc. Cell lines with mutations in the same exon 8 fragment were used to test the method (see, listing in Table 1).

FIG. 3 is a schematic drawing illustrating the use of the RBS60 reference blocking sequence in connection with modified, full COLD-PCR enrichment. An 87 bp amplicon is preliminarily amplified using the underlined primers. The complementary reference blocking sequence (RBS60) is designed for the reference strand in FIG. 3. As apparent from FIG. 3 RBS60 prevents the primers from binding, and contains a 3' phosphate group to prevent extension.

Protocol for RBS60: A 167 bp sequence from p53 exon 8 was initially amplified using conventional PCR and the primers Ex8-1671F and Ex8-167R (Table 1). The genomic DNA used was either wild-type DNA, or a mixture of 3% mutant DNA into wild-type DNA. The mutant cell lines used, that contain specific mutations, are listed in Table 1.

The PCR product was then diluted 500-fold. Then, the modified full-COLD-PCR reaction in the presence of 25 nM reference blocking sequence RBS60, and 200 nM primers 87f and 87r that amplify a region nested within the 167 bp fragment was implemented. Phusion™ polymerase (New England Biolabs) was used for the amplification. The full-COLD-PCR program was: 5 cycles of conventional PCR (30 sec at 95° C.; 30 sec 60° C.; 1 min 72° C.); then 25 cycles of full COLD-PCR (30 sec at 95° C.; 30 sec at 70° C.; then 3 sec at $T_c$=84.5° C., then 30 sec at 60° C.; 1 min at 72° C.)×25. Alternatively, full COLD-PCR (in the absence of RBS60) was performed by applying the exact same program as for full COLD-PCR in the presence of RBS60, but by omitting the RBS60 from the reaction mixture. Following full COLD-PCR in the presence of RBS60 (and full COLD-PCR (no RBS60) and fast COLD-PCR, and regular PCR) the products were sequenced by using the longer primer 30T-p53-87F.

Protocol for RBSS90: The same procedure was applied for RBS90 as detailed for RBS60; but with the difference that the primers set for the nested full COLD-PCR were p53-ex8-115F and p53-ex8-115R and the $T_c$ applied for RBS90 was $T_c$=84.4° C.

TABLE 1

| Oligo | Sequence (5' to 3') | Source |
|---|---|---|
| Reference Blocking Sequence 1 (RBS60) | | |
| Ex8-167F | GCTTCTCTTTTCCTATCCTG (SEQ ID NO: 1) | Li et al (2008) |
| Ex8-167R | CTTACCTCGCTTAGTGCT (SEQ ID NO: 2) | Li et al (2008) |
| 87f | TGGTAATCTACTGGGACG (SEQ ID NO: 3) | Li et al (2008) |
| 87r | CGGAGATTCTCTTCCTCT (SEQ ID NO: 4) | Li et al (2008) |
| 30T-p53-87F | TTTTTTTTTTTTTTTTTTTTTTTTTTTTTTGGTAATCTAC TGGGACG (SEQ ID NO: 5) | |
| 60refseq-for | GGACGGAACAGCTTT (SEQ ID NO: 6) | |
| 60refseq-rev | CTGGCCGCGTGTCT (SEQ ID NO: 7) | |
| RBS60 | 5'CTCTGTGCGCCGGTCTCTCCCAGGACAGGCACAAA CA CGCACCTCAAAGCTGTTCCGTCC-phos-3' (SEQ ID NO: 8) | |
| Reference Blocking Sequence 2 (RBS90) | | |
| Ex8-167F | GCTTCTCTTTTCCTATCCTG (SEQ ID NO: 9) | Li et al (2008) |
| Ex8-167R | CTTACCTCGCTTAGTGCT (SEQ ID NO: 10) | Li et al (2008) |
| p53-ex8-115F | TTGCTTCTCTTTTCCTAT (SEQ ID NO: 11) | |
| p53-ex8-115R | TTTTTTTTTTTTTTTTTTTTTTTTTTTTTTTTTT TTGCTTCTCTTTTCCTATCC (SEQ ID NO: 12) | |
| R8S90 | 5'CTTCCTCTGTGCGCCGGTCTCTCCCAGGACAGGCA CAAACACGCACCTCAAAGCTGTTCCGTCCCAGTAG ATTAC CACTACTCAGGATAG-phos-3' (SEQ ID NO: 13) | |

Results: Representative results are depicted in FIGS. 4 through 7 for the RBS60 and FIG. 8 for RBS90. In FIGS. 4 through 7, modified, full COLD-PCR (in presence of RBS60 is compared with full COLD-PCR (no RBS60). Fast COLD-PCR, and conventional PCR.

Figure 4:
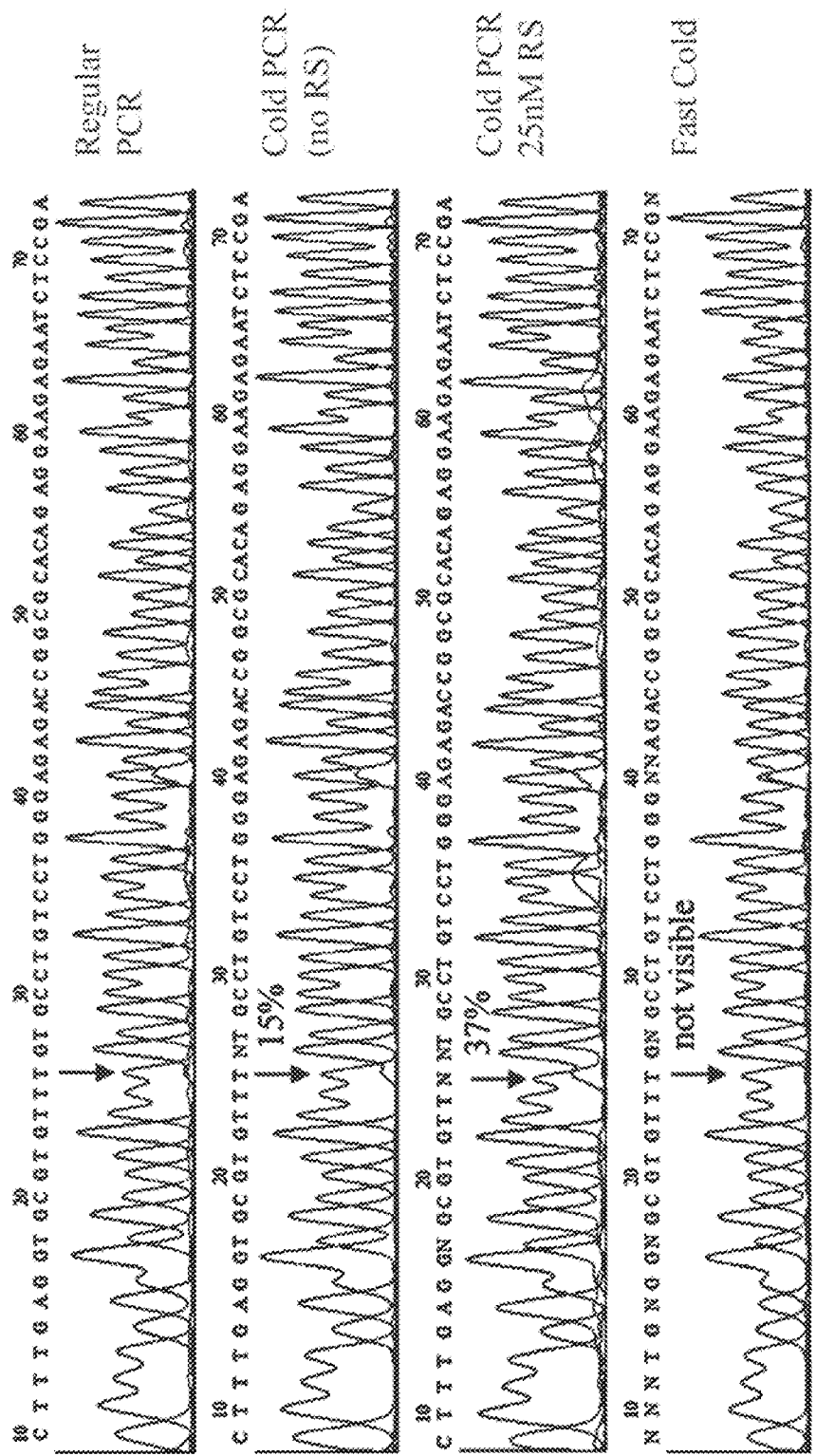
FIG. 4 displays Sanger sequencing data for the enrichment of PFSK-1 mutant alleles from samples processed using regular PCR (SEQ ID NO:16), full COLD PCR without the use of a reference blocking sequence in the reaction mixture (SEQ ID NO:17); full COLD-PCR with an excess of reference blocking sequence in the reaction mixture (SEQ ID NO:18), and fast COLD-PCR (SEQ ID NO:19), respectively.
Figure 5:
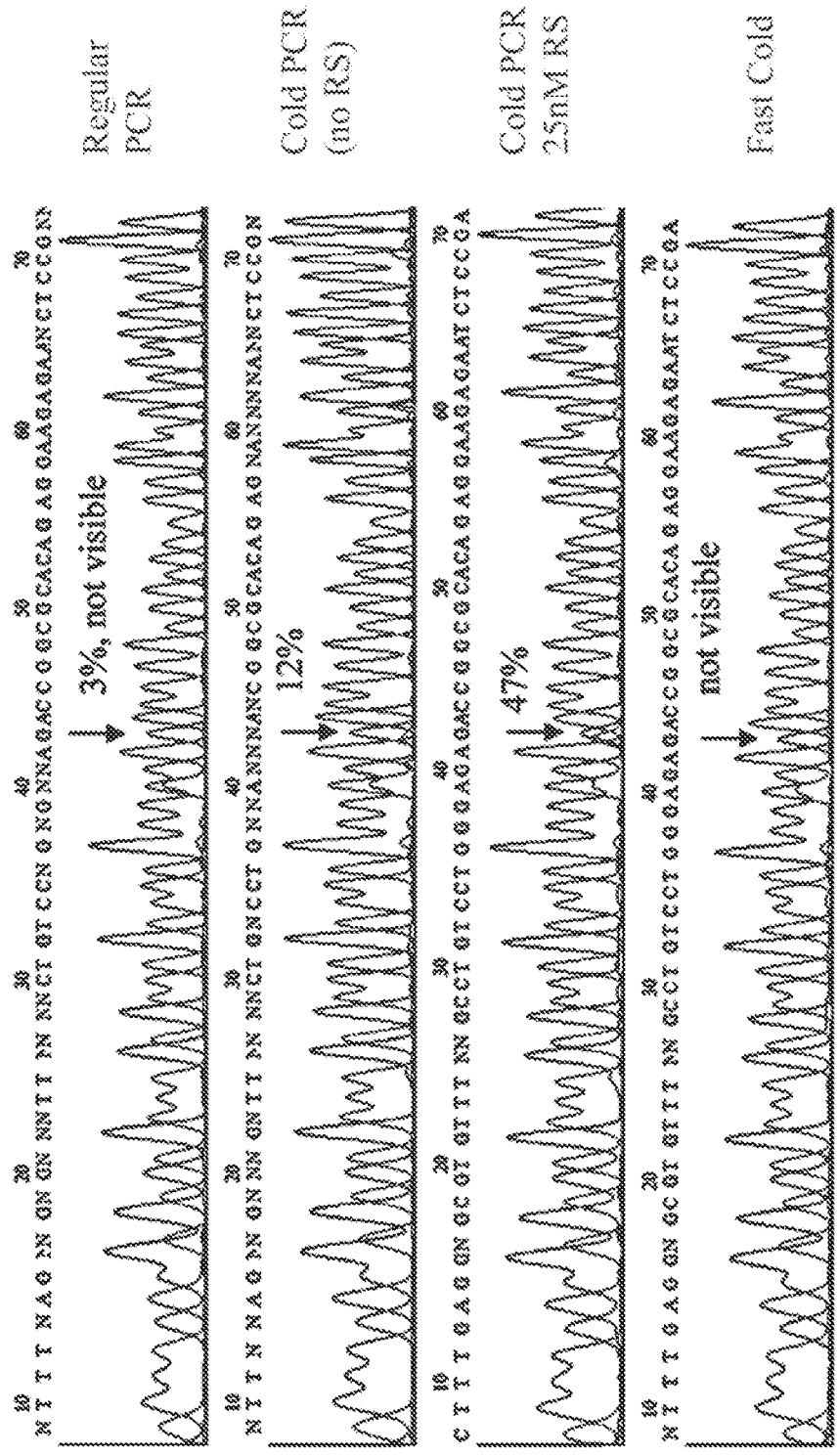
FIG. 5 displays Sanger sequencing data for the enrichment of HCC1008 mutant alleles from samples processed using regular PCR (SEQ ID NO:20), full COLD PCR without the use of a reference blocking sequence in the reaction mixture (SEQ ID NO:21); full COLD-PCR with an excess of reference blocking sequence (RS) (60 bp) in the reaction mixture (SEQ ID NO:22), and fast COLD-PCR (SEQ ID NO:23), respectively.

FIG. 4 illustrates that enrichment via modified full COLD-PCR (25 nM RBS) is robust (an increase from 3% to 37%) for a circumstance in which the mutation increases the melting temperature. The mutation is not detectable when using fast COLD-PCR and conventional PCR in FIG. 4. FIG. 5 similarly illustrates that enrichment via modified full COLD-PCR (25 nM RBS) is robust (an increase from 3% to 47%) for a circumstance in which the mutation does not effect melting temperature. Again, the mutation is not detectable when using fast COLD-PCR and conventional PCR in FIG. 5. FIG. 6 also illustrates that enrichment via modified full COLD-PCR (25 nM RBS) is robust (an increase from 3% to 45%) for a circumstance in which the mutation reduces inciting temperature. In FIG. 6, enrichment via fast COLD-PCR is robust as well (i.e., due to the reduced melting temperature). Again, in FIG. 6, the mutation is not detectable when using conventional PCR. FIG. 7 illustrates the results for a temperature reducing deletion. Enrichment via modified full COLD-PCR (25 nM RBS) is robust (an increase from 3% to 45%) as is enrichment via fast COLD-PCR. Again, the mutation is not detectable when using conventional PCR.

FIG. 8 displays Sanger sequencing data for the enrichment of HCC1008 mutant alleles from samples processed using RBS90, and illustrates that enrichment with modified full COLD-PCR in the presence of the 90 bp reference blocking sequence is robust an increase from 3% to 38%). Comparing the results in FIG. 5, which displays Sanger sequencing data for the enrichment of HCC1008 mutant alleles from samples processed using RBS60, to the results in FIG. 8 confirms that the method of the present invention is robust with reference blocking sequences of different lengths. In all cases and for all mutations studied thus far, modified full COLD-PCR (in presence of RBS) appears to have the best performance, in that it enriches all types of mutations ($T_m$ increasing, retaining or decreasing mutations), in a short reaction time, and with better enrichment than Full-COLD-PCR (no RBS).

I claim:

1. A method for enriching a target nucleic acid sequence in an amplification reaction mixture, said method comprising:
   a) preparing an amplification reaction mixture including at least the following constituents:
      a nucleic acid sample having a reference sequence and also suspected of having one or more target sequences that contain 1-10 nucleotide sequence changes relative to said reference sequence and are also amplifiable by the same primer pair as said reference sequence, and
      an excess amount of reference blocking nucleic acid sequence which is fully complementary with at least a portion of the sequence of one of the strands of the reference sequence between its primer sites;
   b) subjecting the reaction mixture suspected of having said target sequence to a first denaturing temperature that is above the melting temperature ($T_m$) of the reference sequence so as to form denatured reference strands and denatured target strands;
   c) reducing the temperature of the reaction mixture so as to permit formation of heteroduplexes of the reference blocking sequence and the complementary reference strand and heteroduplexes of the reference blocking sequence and target strands;
   d) subjecting said reaction mixture to a critical temperature ($T_c$) sufficient to permit preferential denaturation of said heteroduplexes of the reference blocking sequence and target strands, yet insufficient to denature heteroduplexes of the reference blocking sequence and the complementary reference strand;
   e) reducing the temperature of the reaction mixture so as to permit said primer pair to anneal to free target strands and any free reference strands in the reaction mixture; and
   f) extending said primer pair so as to enrich said target sequence relative to said reference sequence.

2. The method of claim 1 wherein a 3'-end on the reference blocking sequence is blocked to inhibit extension.

3. The method of claim 1 wherein a 5'-end on the reference blocking sequence strands comprises a nucleotide that prevents 5' to 3' exonucleolysis by Taq DNA polymerases.

4. The method of claim 1 wherein the reference blocking sequence in step a) is a single-stranded nucleic acid reference blocking sequence.

5. The method of claim 1 wherein the reference blocking sequence in step a) is a double-stranded nucleic acid reference blocking sequence which denatures to form single strand reference blocking sequences in step b) when the reaction mixture is subject to the first denaturing temperature.

6. The method of claim 1 wherein the reference blocking sequence is one of single stranded DNA, RNA, peptide nucleic acid, locked nucleic acid, or chimera between single stranded DNA, RNA, peptide nucleic acid or locked nucleic acid or another modified nucleotide.

7. The method of claim 1 wherein the reference blocking sequence is fully complementary with one of the strands of the reference sequence between its primer binding sites, or overlapping at either end the primer binding sites.

8. The method of claim 1 wherein the reference blocking sequence is of equal length or shorter than the reference sequence.

9. The method of claim 1 wherein said target sequence comprises a homozygous mutation.

10. The method of claim 1 wherein said target sequence is differentially methylated from the reference sequence, and prior to implementing the method of claim 1 on the reaction mixture, the reaction mixture is treated with sodium bisulfite.

11. The method of claim 1 wherein said reference and target sequences each comprise at least 25 base pairs.

12. The method of claim 1 wherein said method is repeated for two or more cycles.

13. The method of claim 1 further comprising the step of analyzing said reaction mixture with enriched target sequence using one or more of the methods selected from the group consisting of: MALDI-TOF, HR-Melting, Di-deoxy-sequencing, Single-molecule sequencing, pyrosequencing, Second generation high-throughput sequencing, SSCP, RFLP, dHPLC, CCM, digital PCR and quantitative-PCR.

14. The method of claim 1 wherein said $T_c$ is applied for 1 second-60 seconds.

15. The method of claim 1 wherein said reaction mixture contains a nucleic acid detection dye.

16. The method of claim 1 wherein said method is performed in a real-time PCR device.

17. The method of claim 1 performed under real-time reaction conditions utilizing a labeled probe.

18. The method of claim 1, wherein the one or more target sequences contain 1 nucleotide sequence change relative to said reference sequence.

19. The method of claim 18, wherein the one or more target sequence is a mutant allele and the reference sequence is wild-type of the mutant allele.

* * * * *